(12) United States Patent
Engelhardt et al.

(10) Patent No.: US 11,213,520 B2
(45) Date of Patent: Jan. 4, 2022

(54) PHENYLPYRAZOLYLACETAMIDE COMPOUNDS AND DERIVATIVES AS CDK8/CDK19 INHIBITORS

(71) Applicant: BOEHRINGER INGELHEIM INTERNATIONAL GMBH, Ingelheim am Rhein (DE)

(72) Inventors: Harald Engelhardt, Ebreichsdorf (AT); Heribert Arnhof, Vienna (AT); Sebastian Carotta, Vienna (AT); Marco Hans Hofmann, Vienna (AT); Marc Kerenyi, Vienna (AT); Dirk Scharn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/301,218

(22) PCT Filed: May 19, 2017

(86) PCT No.: PCT/EP2017/062107
§ 371 (c)(1),
(2) Date: Nov. 13, 2018

(87) PCT Pub. No.: WO2017/202719
PCT Pub. Date: Nov. 30, 2017

(65) Prior Publication Data
US 2019/0290637 A1    Sep. 26, 2019

(30) Foreign Application Priority Data
May 23, 2016   (EP) ..................................... 16170885

(51) Int. Cl.
| | | |
|---|---|---|
| *A61K 31/4725* | (2006.01) | |
| *A61K 31/4375* | (2006.01) | |
| *C07D 401/10* | (2006.01) | |
| *C07D 401/14* | (2006.01) | |
| *C07D 471/04* | (2006.01) | |

(52) U.S. Cl.
CPC ...... *A61K 31/4725* (2013.01); *A61K 31/4375* (2013.01); *C07D 401/10* (2013.01); *C07D 401/14* (2013.01); *C07D 471/04* (2013.01)

(58) Field of Classification Search
CPC ................................................ A61K 31/4725
USPC ........................................................ 546/112
See application file for complete search history.

(56) References Cited

U.S. PATENT DOCUMENTS 9,957,251 B2    5/2018   Hirayama et al.

FOREIGN PATENT DOCUMENTS

| WO | 2008021781 A1 | 2/2008 | |
| WO | WO 2008064157 | * 5/2008 | ........... C07D 48/704 |
| WO | 2015159938 A1 | 10/2015 | |
| WO | 2016009076 A1 | 1/2016 | |

OTHER PUBLICATIONS

Dorwald F. A. Side Reactions in Organic Synthesis, 2005, Wiley: VCH, Weinheim p. IX of Preface p. 1-15.*
Venkatesh, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
International Search Report for PCT/EP2017/062107 filed May 19, 2017.
Rzymski, Tomasz et al. "CDK8 kinase—An emerging target in targeted cancer therapy" (2015) Biochimica et Biophysica Acta, 1854, 1617-1629.

* cited by examiner

*Primary Examiner* — Nizal S Chandrakumar
(74) *Attorney, Agent, or Firm* — Andrea Lockenour

(57) ABSTRACT

The present invention encompasses compounds of formula (I) wherein the groups $R^2$ to $R^5$, A, X and q have the meanings given in the claims and specification, their use as inhibitors of CDK8/19, pharmaceutical compositions which contain compounds of this kind and their use as medicaments, especially as agents for treatment and/or prevention of oncological diseases.

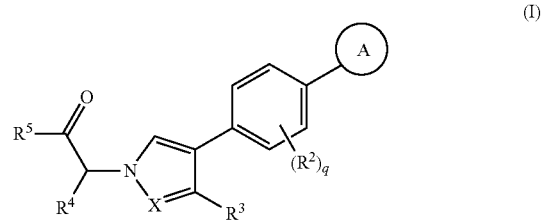

14 Claims, No Drawings

PHENYLPYRAZOLYLACETAMIDE COMPOUNDS AND DERIVATIVES AS CDK8/CDK19 INHIBITORS

FIELD OF THE INVENTION

The present invention relates to new phenylpyrazolylacetamide compounds and derivatives of formula (I)

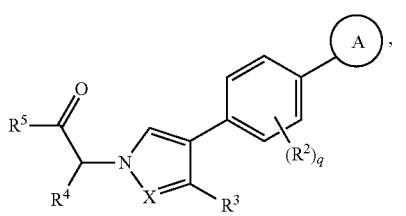

wherein the groups $R^2$ to $R^5$, A, X and q have the meanings given in the claims and specification, their use as inhibitors of CDK8, pharmaceutical compositions which contain compounds of this kind and their use as medicaments, especially as agents for treatment and/or prevention of oncological diseases.

BACKGROUND OF THE INVENTION

CDK8/cyclin C is part of the mediator complex, which consist of four proteins (CDK8, CCNC, MED12 and MED13 (Kagey M H. et al., 2010 Nature 467(7314):430-5; Pelish H E. et al. 2015 Nature 526(7572): 273-276). A high number of substrates which are phosphorylated by CDK8 were identified, for example AFF4, RNA Pol II, STAT1, H2, E2F1, MAML1, MED12, MED13, MED13L, Notch and SMAD (Rzymski T et al. 2015 Biochimica et Biophysica Acta 1854(10 Pt B):1617-29; Poss Z C et al. 2016 Cell 15(2):436-50). Inhibition of CDK8 leads to decreased phosphorylation and gene specific activation and repression (Rzymski T et al. 2015 Biochimica et Biophysica Acta 1854(10 Pt B):1617-29). The kinase and cyclin binding domains of CDK8 and CDK19 (alias of CDK19 is CDK11) show 97% indentity and both enzymes have nearly 80% amino acid sequence indentity (Tsutsui T. 2008 Genes Cell 13(8):817-26).

A cancer cell-directed effect of CDK8 inhibitors was postulated in several publications (Firestein R. et al. 2008 Nature 455(7212):547-51; Pelish H E. et al. 2015 Nature 526(7572): 273-276; Porter D C et al. 2012 PNAS 109(34): 13799-804 and Dale T et al. 2015 Nature Chemical Biology 11(12):973-80). High expression or amplification of CDK8 together with β-catenin hyperactivity has been reported in a subset of colorectal cancers (Firestein R et al. 2008 Nature 455(7212):547-51). CDK8 was reported to act as a colon cancer oncogene necessary for β-catenin activity and suppression of CDK8 using shRNA inhibited proliferation (Firestein R et al. 2008 Nature 455(7212):547-51). CDK8/19 inhibitors reduced phosphorylation of the known CDK8 substrate identical to CDK8 knockout clones (Koehler M F et al. 2016 ACS Medicinal Chemistry Letters 7(3):223-8). In vivo activity of CDK8 inhibitors in WNT dependent tumors was published (Dale T et al. 2015 Nature Chemical Biology 11(12):973-80). A combinatorial anti-tumor effect of CDK8 inhibitors in combination with chemotherapeutic drugs was reported due to suppression of tumor-promoting paracrine activities mediated by the CDK8 inhibitor (Porter D C et al. 2012 PNAS 109(34):13799-804). In case of acute myeloid leukemia (AML) cells it was reported that the Mediator-associated kinases cyclin-dependent kinase 8 (CDK8) and CDK19 restrain increased activation of key super-enhancer-associated genes. Inhibition with a CDK8 inhibitor resulted in inhibition of the Mediator kinases, induced upregulation of super-enhancer associated genes in CDK8 sensitive AML cell lines and led to reduced proliferation and anti-tumor efficacy in vivo (Pelish H E. et al. 2015 Nature 526(7572): 273-276).

Besides the direct effect of CDK8 on tumor cells it is now known that CDK8 mediated STAT1 Ser727 phosphorylation reduces the cytotoxic potential of NK cells (Putz E M et al. 2013 Cell Reports 4(3):437-44). The signal transducer and activator of transcription 1 (STAT1) is activated by JAK-mediated phosphorylation of tyrosine 701, which results in dimerization and nuclear translocation. CDK8 was described to phosphorylate STAT1 at serine 727 and it was shown that reduced phosphorylation of STAT1 at serine 727 result in enhanced translation of granzyme B and perforin and subsequently a higher amount of granzyme B and perforin positive NK cells (Putz E M et al. 2013 Cell Reports 4(3):437-44). In agreement with this, a STAT1 S727A mutant mouse model showed highly activated NK cells and improved NK cell cytotoxicity against hematological diseases and significant improved survival in a B16-F10 melanoma mouse model (Putz E M et al. 2013 Cell Reports 4(3):437-44). Natural killer (NK) cells play critical roles in host immunity against cancer. In contrast to T cells, NK cells rapidly kill certain target cells without prior immunization or MHC restriction. NK cell activity is tightly regulated by cytokines, activating and inhibitory receptors. It is well known that the existing NK cells in the tumor microenvironment are often hyporesponsive (Frassanito M A et al. 1997 International Journal of Clinical and Laboratory Research 27(1):48-54; Hejazi M et al. 2015 Heamatologica 100(5):643-52) due to down regulation of activating receptors or upregulation of inhibitory signals. Several studies have demonstrated that NK cell numbers are increased in patients with low tumor burden. However, NK cell mediated tumor surveillance declines during the progression of the disease. Patients show higher number of NK cells but with impaired function (Benson D M Jr et al. 2015 Clinical Cancer Research 21(18):4055-61; Frassanito M A et al. 1997 International Journal of Clinical and Laboratory Research 27(1):48-54; Hejazi M et al. 2015 Heamatologica 100(5): 643-52). Over the last decades several approaches have been developed to utilize NK cells to treat multiple myeloma (MM) (Godfrey J et al. 2012 Leukemia & Lymphoma 53(9):1666-76 and Cheng M et al. 2013 Cellular & Molecular Immunology 10(3):230-52). NK cell-mediated immunotherapy is not limited to multiple myeloma and NK cell therapies are currently tested in other hematological cancers, especially acute myeloid leukemia (AML), as well as in solid tumors (Childs R W et al. 2015 Nature Reviews 14(7):487-98).

The following prior art documents disclose compounds as CDK8 inhibitors: WO 2013/001310, WO 2013/040153, WO 2013/116786, US 2012/071477, WO 2014/134169, WO 2014/029726, WO 2014/106606, WO 2014/090692, WO 2014/154723, WO 2015/049325, WO 2014/072435, WO 2014/194201, WO 2014/194245, WO 2015/159937, WO 2014/123900, WO 2015/100420, WO 2014/063778, WO 2015/144290, WO 2016/009076, WO 2016/026549.

Although the compounds from the above mentioned documents are claimed as CDK8 inhibitors, most of them also display affinity to other CDK family members (in addition to CDK19). In addition, the observed CDK8 mediated reduction of the pSTAT1 Ser727 levels in cells is often only moderate (e.g. compounds from WO 2014/072435, WO 2014/134169, WO 2013/040153, WO 2013/116786, US 2012/071477, WO2016/009076). Furthermore, the overall selectivity profile of these compounds is often not acceptable (e.g. compounds disclosed in WO 2015/144290 and Dale et al., Nat. Chem. Biol. (2015) 11: 973 inhibit GSK3a and GSK3b with an $IC_{50}<1$ μM; WO2014/090692, WO 2014/154723, WO 2014/106606, WO 2014/072435 and WO 2014/029726). This modest kinase selectivity results in an unspecific (CDK8 inhibition independent) cytotoxic behavior in several cell based proliferation assays (e.g. NK-92 cells, A549 cells and B16-F10 cells). This unspecific cytotoxic component is undesirable, because it potentially leads to adverse events in treated patients.

Furthermore, due to unfavorable DMPK properties of the prior art CDK8 inhibitors, high doses are necessary for in vivo experiments or these experiments are even not feasible. Consequently, it is unlikely that these CDK8 inhibitors can be applied to humans (WO 2014/072435, WO 2014/134169, WO 2016/009076, WO 2014/072435).

The aim of the present invention is to provide selective and potent compounds which may be used to inhibit the kinase function of CDK8 and CDK19. Inhibition of CDK8 and CDK19 may result in reduction of phosphorylation of STAT1 at the position Ser727 in NK cells which may lead to increased expression levels and an increased number of granzyme B and perforin positive NK cells (i.e. increased secretion of granzyme B and perforin). The increased NK cell activity may translate in increased tumor cell killing, improved tumor surveillance and prolonged survival in cancer patients. The same concept could also apply to other immune cells like cytotoxic T-lymphocytes (CTL). Furthermore a direct cancer cell-directed effect of CDK8 inhibitors holds true in some indications (for example AML; Pelish H E. et al. 2015 Nature 526(7572): 273-276). Accordingly, CDK8 inhibitors may offer an important approach towards cancer therapy either as single agent or in combination with a broad variety of anti-tumor therapies or agents for activation of the immune system which may be used for treatment of hematological disease (for example AML, MM, myelodysplastic syndromes (MDS) and chronic lymphocytic leukemia (CLL)) but also for the treatment of solid tumors.

In addition to the inhibitory effect and potency, compounds disclosed herein show good solubility, fine-tuned DMPK properties and excellent selectivity over other kinases of the human kinome.

DETAILED DESCRIPTION OF THE INVENTION

It has now been found that, surprisingly, compounds of formula (I) wherein the groups $R^2$ to $R^5$, A, X and q have the meanings given hereinafter act as inhibitors of CDK8 which are involved in controlling cell proliferation. Thus, the compounds according to the invention may be used for example for the treatment of diseases characterised by excessive or abnormal cell proliferation.

The present invention therefore relates to a compound of formula (I)

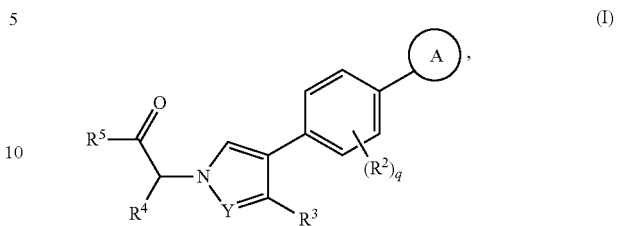

wherein
[A0]
ring system A is selected from the group consisting of A1 and A2

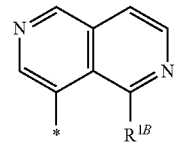

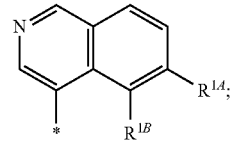

$R^{1A}$ is selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;

each $R^{1B}$ is independently selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;
or
$R^{1A}$ together with $R^{1B}$ and the atoms they are linked to form a 5-6 membered heteroaryl;
[B0]
each $R^2$ is independently selected from the group consisting of halogen, $C_{1-4}$alkyl, $C_{1-4}$haloalkyl and $C_{1-4}$alkoxy;
q has the value 0, 1 or 2;
[C0]
Y is CH or N;
[D0]
$R^3$ is selected from the group consisting of hydrogen, halogen, $C_{1-4}$alkyl and $C_{1-4}$haloalkyl;
[E0]
$R^4$ is selected from the group consisting of hydrogen and $C_{1-4}$alkyl;
$R^5$ is selected from the group consisting of —$NR^{5A}R^{5B}$, —$OR^{5C}$ and $R^{5D}$;
$R^{5A}$, $R^{5B}$ and $R^{5C}$, each independently of one another, denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$, —$N(C_{1-4}alkyl)C(O)R^{c1}$ and the bivalent substituent =O, while =O may only be a substituent in non-aromatic ring systems;

each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

or $R^{5A}$ together with $R^4$ or $R^{5C}$ together with $R^4$ is $C_{1-5}$alkylene and $R^{5B}$ is selected from among hydrogen and $C_{1-4}$alkyl;

$R^{5D}$ denotes a 3-10 membered nitrogen containing heterocyclyl linked via a nitrogen atom and optionally substituted by one or more, identical or different $R^{b2}$ and/or $R^{c2}$;

each $R^{b2}$ is independently selected from among —$OR^{c1}$, —$NR^{c1}R^{c1}$, halogen, —CN, —$C(O)R^{c2}$, —$C(O)OR^{c2}$, —$C(O)NR^{c2}R^{c2}$, —$S(O)_2R^{c2}$, —$S(O)_2NR^{c2}R^{c2}$, —$NHC(O)R^{c2}$, —$N(C_{1-4}alkyl)C(O)R^{c2}$ and the bivalent substituent =O;

each $R^{c2}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

or a salt thereof.

In one aspect [A1] the invention relates to a compound of formula (I), wherein ring system A is A1

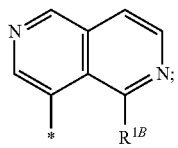

A1

$R^{1B}$ is independently selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alky, —CN and 5-6 membered heteroaryl;

or a salt thereof.

In another aspect [A2] the invention relates to a compound of formula (I), wherein ring system A is A1

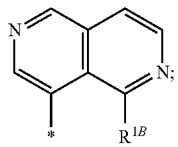

A1

$R^{1B}$ is hydrogen;

or a salt thereof.

In another aspect [A3] the invention relates to a compound of formula (I), wherein ring system A is A2

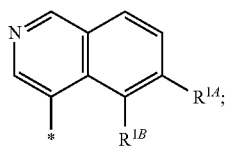

A2

$R^{1A}$ is independently selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;

$R^{1B}$ is independently selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;

or $R^{1A}$ together with $R^{1B}$ and the atoms they are linked to form a 5-6 membered heteroaryl;

or a salt thereof.

In another aspect [A4] the invention relates to a compound of formula (I), wherein ring system A is A2

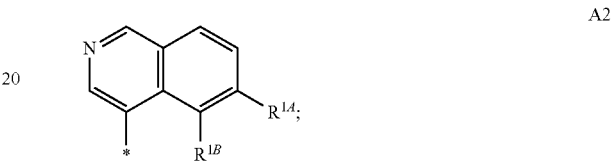

A2

$R^{1A}$ is independently selected from the group consisting of hydrogen and hydroxy-$C_{1-4}$alkyl;

$R^{1B}$ is hydrogen;

or a salt thereof.

In another aspect [B1] the invention relates to a compound of formula (I), wherein q is 0;

or a salt thereof.

In another aspect [C1] the invention relates to a compound of formula (I), wherein Y is CH;

or a salt thereof.

In another aspect [C2] the invention relates to a compound of formula (I), wherein Y is N;

or a salt thereof.

In another aspect [D1] the invention relates to a compound of formula (I), wherein $R^3$ is selected from the group consisting of hydrogen, halogen and $C_{1-4}$alkyl;

or a salt thereof.

In another aspect [D2] the invention relates to a compound of formula (I), wherein $R^3$ is selected from the group consisting of hydrogen, chlorine and methyl;

or a salt thereof.

In another aspect [E1] the invention relates to a compound of formula (I), wherein $R^4$ is selected from the group consisting of hydrogen and $C_{1-4}$alkyl;

$R^5$ is —$OR^{5C}$;

$R^{5C}$ denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2NR^{c1}R^{c1}$, —$NHC(O)R^{c1}$, —$N(C_{1-4}alkyl)C(O)R^{c1}$ and the bivalent substituent =O, while =O may only be a substituent in non-aromatic ring systems;

each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5C}$ together with $R^4$ is $C_{1-5}$alkylene;
or a salt thereof.

In another aspect [E2] the invention relates to a compound of formula (I), wherein
$R^4$ is selected from the group consisting of hydrogen and $C_{1-4}$alkyl;
$R^5$ is —$OR^{5C}$;
$R^{5C}$ denotes hydrogen or $C_{1-6}$alkyl;
or
$R^{5C}$ together with $R^4$ is $C_{1-5}$alkylene;
or a salt thereof.

In another aspect [E3] the invention relates to a compound of formula (I), wherein
$R^4$ is selected from the group consisting of hydrogen and $C_{1-4}$alkyl;
$R^5$ is —$OR^{5C}$;
$R^{5C}$ denotes hydrogen or $C_{1-6}$alkyl;
or a salt thereof.

In further aspects [E4], [E5], [E6] and [E7] the invention relates to a compound of formula (I) with structural aspects [E0], [E1], [E2] and [E3], wherein
$R^4$ is selected from the group consisting of hydrogen and methyl;
or a salt thereof.

In further aspects [E8], [E9], [E10] and [E1] the invention relates to a compound of formula (I) with structural aspects [E0], [E1], [E2] and [E3], wherein
$R^4$ is hydrogen;
or a salt thereof.

In another aspect [E12] the invention relates to a compound of formula (I), wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
   each $R^{b1}$ is independently selected from among —$OR^{c1}$, —$NR^{c1}R^{c1}$, halogen, —CN, —C(O)$R^{c1}$, —C(O)$OR^{c1}$, —C(O)$NR^{c1}R^{c1}$, —S(O)$_2R^{c1}$, —S(O)$_2NR^{c1}R^{c1}$, —NHC(O)$R^{c1}$, —N($C_{1-4}$alkyl)C(O)$R^{c1}$ and the bivalent substituent =O, while =O may only be a substituent in non-aromatic ring systems;
   each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5A}$ together with $R^4$ is $C_{1-5}$alkylene and $R^{5B}$ is selected from among hydrogen and $C_{1-4}$alkyl;
or a salt thereof.

In another aspect [E13] the invention relates to a compound of formula (I), wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by one or more, identical or different $R^{b1}$ and/or $R^{c1}$, selected from among $C_{1-6}$alkyl and 3-10 membered heterocyclyl;
   each $R^{b1}$ is independently selected from among —$OR^{c1}$, —$NR^{c1}R^{c1}$, halogen, —CN, —C(O)$R^{c1}$, —C(O)$OR^{c1}$, —C(O)$NR^{c1}R^{c1}$, —S(O)$_2R^{c1}$, —S(O)$_2NR^{c1}R^{c1}$, —NHC(O)$R^{c1}$, —N($C_{1-4}$alkyl)C(O)$R^{c1}$ and the bivalent substituent =O, while =O may only be a substituent in non-aromatic ring systems;
   each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5A}$ together with $R^4$ is $C_{1-5}$alkylene and $R^{5B}$ is selected from among hydrogen and $C_{1-4}$alkyl;
or a salt thereof.

In another aspect [E14] the invention relates to a compound of formula (I), wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by $C_{1-6}$alkyl, selected from among $C_{1-6}$alkyl and 3-10 membered heterocyclyl;
or
$R^{5A}$ together with $R^4$ is $C_{1-5}$alkylene and $R^{5B}$ is selected from among hydrogen and $C_{1-4}$alkyl;
or a salt thereof.

In another aspect [E15] the invention relates to a compound of formula (I), wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by $C_{1-6}$alkyl, selected from among $C_{1-6}$alkyl and 3-10 membered heterocyclyl;
or a salt thereof.

In further aspects [E16], [E17], [E18] and [E19] the invention relates to a compound of formula (I) with structural aspects [E12], [E13], [E14] and [E15], wherein $R^4$ is selected from the group consisting of hydrogen and methyl;
or a salt thereof.

In further aspects [E20], [E21], [E22] and [E23] the invention relates to a compound of formula (I) with structural aspects [E12], [E13], [E14] and [E15], wherein
$R^4$ is hydrogen;
or a salt thereof.

In another aspect [E24] the invention relates to a compound of formula (I), wherein
$R^4$ is selected from the group consisting of hydrogen and $C_{1-4}$alkyl;
$R^5$ is $R^{5D}$;
$R^{5D}$ denotes a 3-10 membered nitrogen containing heterocyclyl linked via a nitrogen atom and optionally substituted by one or more, identical or different $R^{b2}$ and/or $R^{c2}$;
   each $R^{b2}$ is independently selected from among —$OR^{c1}$, —$NR^{c1}R^{c1}$, halogen, —CN, —C(O)$R^{c2}$, —C(O)$OR^{c2}$, —C(O)$NR^{c2}R^{c2}$, —S(O)$_2R^{c2}$, —S(O)$_2NR^{c2}R^{c2}$, —NHC(O)$R^{c2}$, —N($C_{1-4}$alkyl)C(O)$R^{c2}$ and the bivalent substituent =O;
   each $R^{c2}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or a salt thereof.

In another aspect [E25] the invention relates to a compound of formula (I), wherein
$R^4$ is selected from the group consisting of hydrogen and $C_{1-4}$alkyl;
$R^5$ is $R^{5D}$;
$R^{5D}$ denotes a 5-7 membered nitrogen containing heterocyclyl linked via a nitrogen atom and optionally substituted by one or more, identical or different $R^{b2}$ and/or $R^{c2}$;
  each $R^{b2}$ is independently selected from among —$OR^{c1}$, —$NR^{c1}R^{c1}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$, —N($C_{1-4}$alkyl)C(O)$R^{c2}$ and the bivalent substituent =O;
  each $R^{c2}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or a salt thereof.

In another aspect [E26] the invention relates to a compound of formula (I), wherein
$R^4$ is selected from the group consisting of hydrogen and $C_{1-4}$alkyl;
$R^5$ is $R^{5D}$;
$R^{5D}$ denotes a 5-7 membered nitrogen containing heterocyclyl linked via a nitrogen atom and optionally substituted by $C_{1-6}$alkyl;
or a salt thereof.

In further aspects [E27], [E28] and [E29] the invention relates to a compound of formula (I) with structural aspects [E24], [E25] and [E26], wherein
$R^4$ is selected from the group consisting of hydrogen and methyl;
or a salt thereof.

In further aspects [E30], [E31] and [E32] the invention relates to a compound of formula (I) with structural aspects [E24], [E25] and [E26], wherein
$R^4$ is hydrogen;
or a salt thereof.

In another aspect [E33] the invention relates to a compound of formula (I), wherein
$R^4$ is selected from the group consisting of hydrogen and $C_{1-4}$alkyl;
$R^5$ is N,N-dimethylamino;
or a salt thereof.

In another aspect [E34] the invention relates to a compound of formula (I) with structural aspect [E33], wherein
$R^4$ is selected from the group consisting of hydrogen and methyl;
or a salt thereof.

In another aspect [E35] the invention relates to a compound of formula (I) with structural aspect [E33], wherein
$R^4$ is hydrogen;
or a salt thereof.

All the above-mentioned structural aspects [A1] to [A4], [B1], [C1] and [C2], [D1] and [D2] and [E1] to [E35] are preferred embodiments of the corresponding aspects [A0], [B0], [C0], [D0] and [E0], respectively. The structural aspects [A0] to [A4], [B0] and [B1], [C0] to [C2], [D0] to [D2] and [E0] to [E35] relating to different molecular parts of the compounds (I) according to the invention may be permutated with one another as desired in combinations [A][B][C][D][E], so as to obtain preferred compounds (I). Each combination [A][B][C][D][E] represents and defines individual embodiments or generic subsets of compounds (I) according to the invention.

Preferred embodiments of the invention with structure (I) are example compounds I-001 to I-017.

All synthetic intermediates generically defined as well es specifically disclosed herein and their salts are also part of the invention.

The present invention further relates to hydrates, solvates, polymorphs, metabolites, derivatives, isomers and prodrugs of a compound of formula (I).

Compounds of formula (I) which e.g. bear ester groups are potential prodrugs the ester being cleaved under physiological conditions.

The present invention further relates to a pharmaceutically acceptable salt of a compound of formula (I).

The present invention further relates to a co-crystal, preferably a pharmaceutically acceptable co-crystal, of a compound of formula (I).

The present invention further relates to a pharmaceutically acceptable salt of a compound of formula (I) with anorganic or organic acids or bases.

The present invention is directed to compounds of formula (I) which are useful in the prevention and/or treatment of a disease and/or condition wherein the inhibition of the kinase activity of CDK8 is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a compound of formula (I)—or a pharmaceutically acceptable salt thereof—for use in the treatment and/or prevention of a disease and/or condition wherein the inhibition of the kinase activity of CDK8 is of therapeutic benefit.

In another aspect the invention relates to a compound of formula (I)—or a pharmaceutically acceptable salt thereof—for use in the treatment and/or prevention of cancer, infections, inflammations or autoimmune diseases.

In another aspect the invention relates to a compound of formula (I)—or a pharmaceutically acceptable salt thereof—for use in a method of treatment and/or prevention of cancer, infections, inflammations or autoimmune diseases in the human or animal body.

In another aspect the invention relates to the use of a compound of formula (I)—or a pharmaceutically acceptable salt thereof—for preparing a pharmaceutical composition for the treatment and/or prevention of cancer, infections, inflammations or autoimmune diseases.

In another aspect the invention relates to a compound of formula (I)—or a pharmaceutically acceptable salt thereof—for use in the treatment and/or prevention of cancer.

In another aspect the invention relates to the use of a compound of formula (I)—or a pharmaceutically acceptable salt thereof—for preparing a pharmaceutical composition for the treatment and/or prevention of cancer.

In another aspect the invention relates to a compound of formula (I)—or a pharmaceutically acceptable salt thereof—for use in a method of treatment and/or prevention of cancer in the human or animal body.

In another aspect the invention relates to a compound of formula (I)—or a pharmaceutically acceptable salt thereof—for use in the treatment and/or prevention of a hematological cancer.

In another aspect the invention relates to a compound of formula (I)—or a pharmaceutically acceptable salt thereof—for use in the treatment and/or prevention of diffuse large cell lymphoma (DLCL), acute myeloid leukemia (AML), chronic lymphatic leukemia (CLL), multiple myeloma (MM) or myelodysplastic syndrome (MDS).

In another aspect the invention relates to the use of a compound of formula (I)—or a pharmaceutically acceptable salt thereof—for preparing a pharmaceutical composition for the treatment and/or prevention of a hematological cancer.

In another aspect the invention relates to the use of a compound of formula (I)—or a pharmaceutically acceptable salt thereof—for preparing a pharmaceutical composition for the treatment and/or prevention of diffuse large cell lymphoma (DLCL), acute myeloid leukemia (AML), chronic lymphatic leukemia (CLL), multiple myeloma (MM) or myelodysplastic syndrome (MDS).

In another aspect the invention relates to a method for the treatment and/or prevention of a disease and/or condition wherein the inhibition of the kinase activity of CDK8 is of therapeutic benefit comprising administering a therapeutically effective amount of a compound of formula (I)—or a pharmaceutically acceptable salt thereof—to a human being.

In another aspect the invention relates to a method for the treatment and/or prevention of cancer comprising administering a therapeutically effective amount of a compound of formula (I)—or a pharmaceutically acceptable salt thereof—to a human being.

In another aspect the invention relates to a pharmaceutical composition comprising at least one compound of formula (I)—or a pharmaceutically acceptable salt thereof—and a pharmaceutically acceptable carrier.

In another aspect the invention relates to a pharmaceutical preparation comprising a compound of formula (I)—or a pharmaceutically acceptable salt thereof—and at least one other cytostatic and/or cytotoxic active substance.

In another aspect the invention relates to a compound of formula (I)—or a pharmaceutically acceptable salt thereof—for use in the treatment and/or prevention of cancer, infections, inflammations or autoimmune diseases wherein said compound is administered before, after or together with at least one other cytostatic or cytotoxic active substance.

In another aspect the invention relates to the use of a compound of formula (I)—or a pharmaceutically acceptable salt thereof—for preparing a medicament for the treatment and/or prevention of cancer, infections, inflammations or autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I)—or a pharmaceutically acceptable salt thereof—for use in the treatment and/or prevention of cancer, infections, inflammations or autoimmune diseases.

In another aspect the invention relates to a method for the treatment and/or prevention of cancer, infections, inflammations or autoimmune diseases comprising administering to a patient in need thereof a therapeutically effective amount of a compound of formula (I)—or a pharmaceutically acceptable salt thereof—before, after or together with at least one other cytostatic or cytotoxic active substance.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CH(CH(CH_3))_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms in common. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0] decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

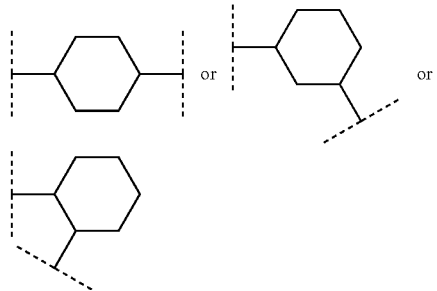

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

cyclopentenyl and

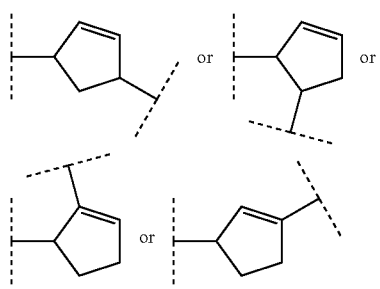

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

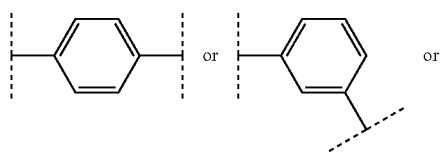

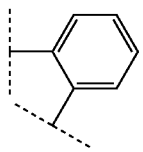

(o, m, p-phenylene), naphthyl and

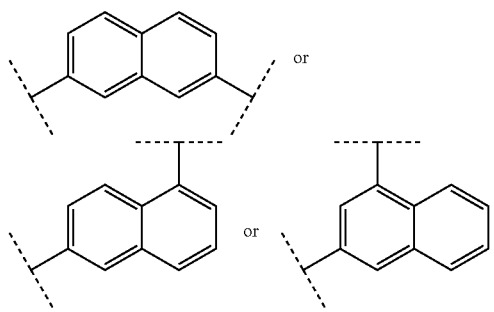

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

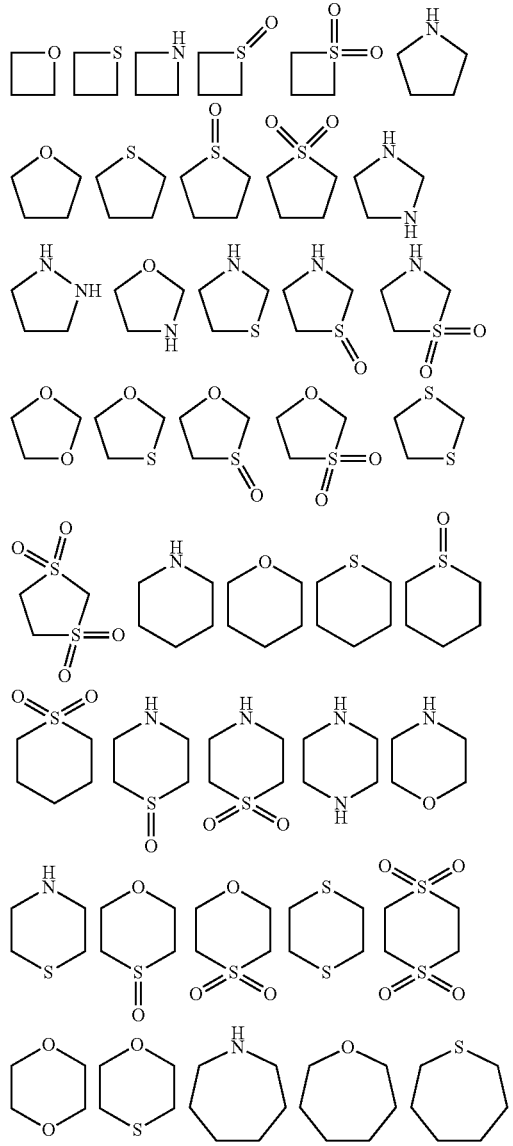

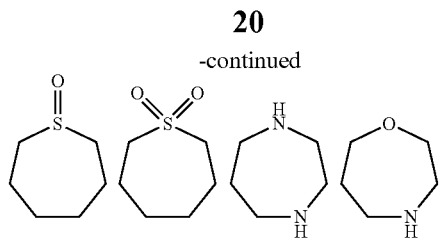
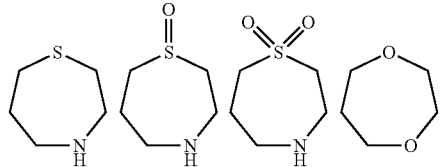
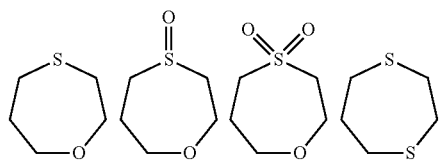
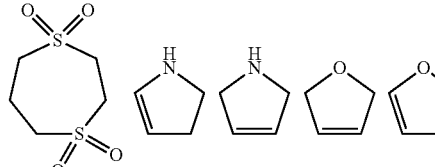
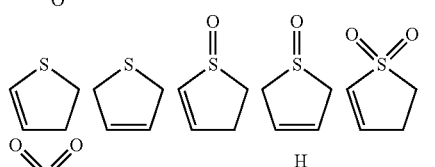
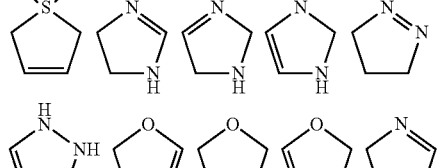
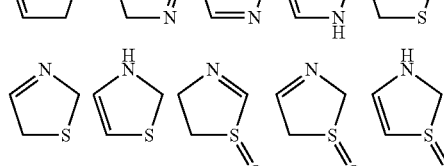
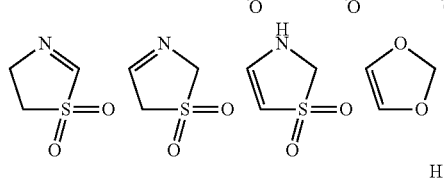
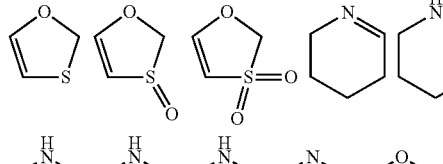
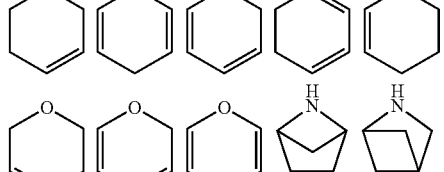

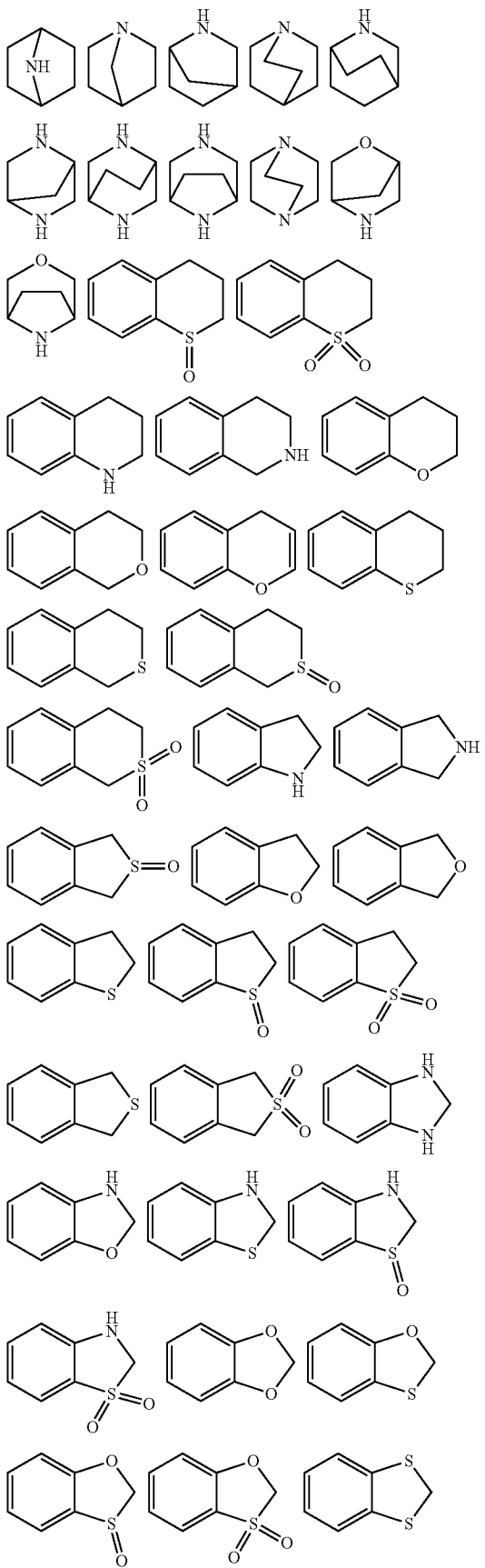
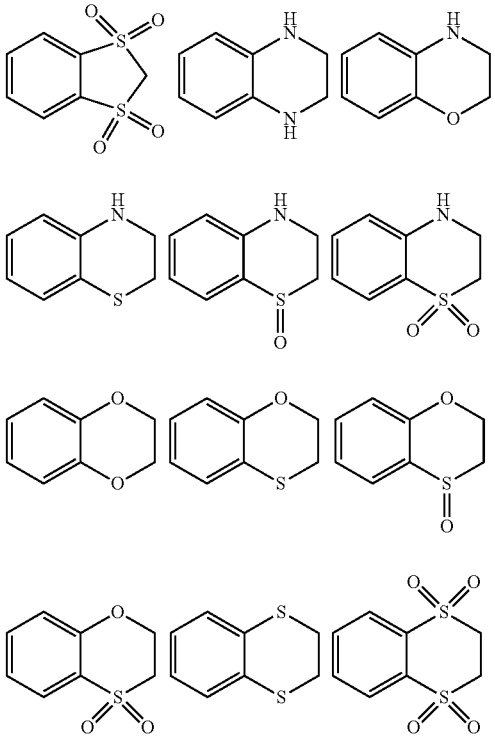

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

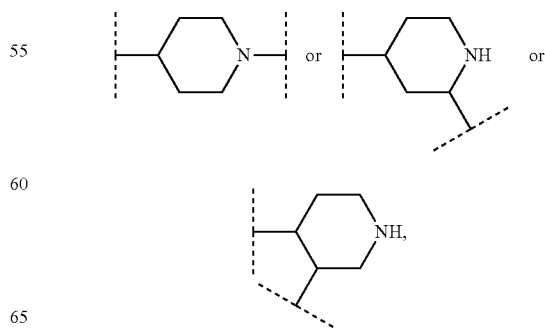

2,3-dihydro-1H-pyrrolyl and

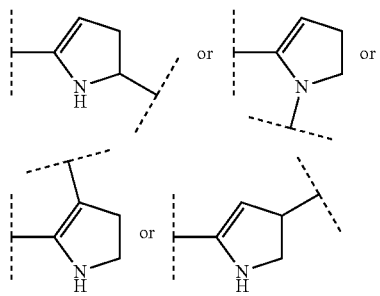

etc.

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

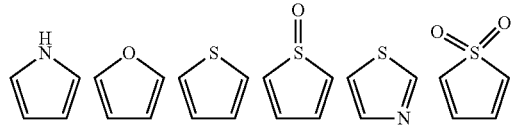

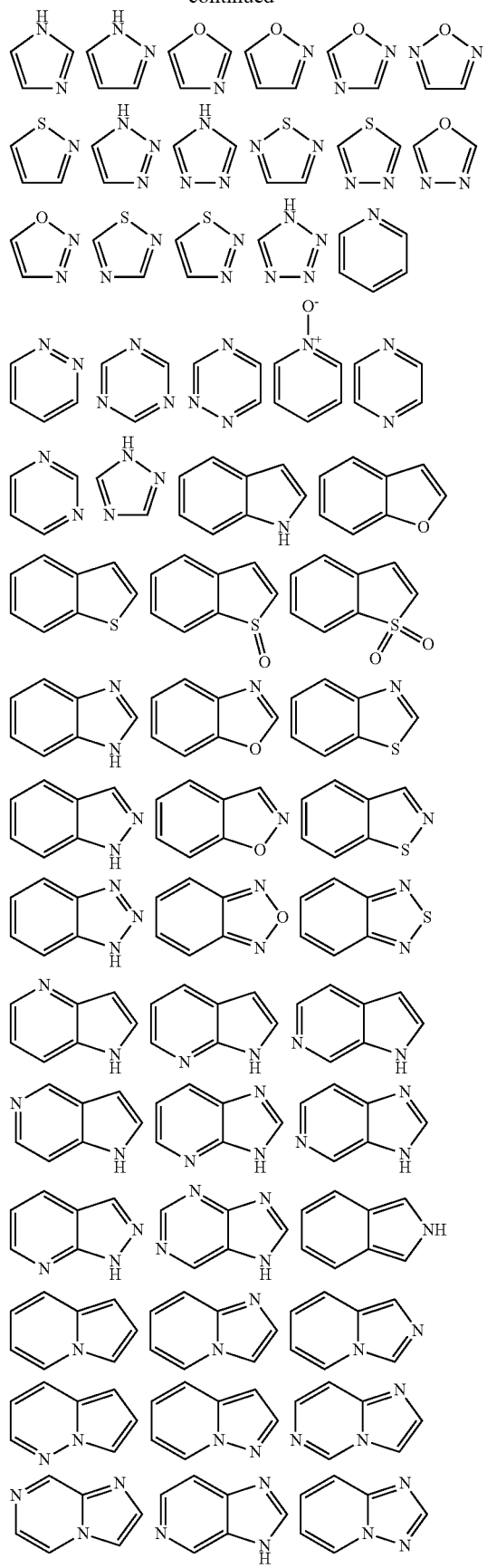

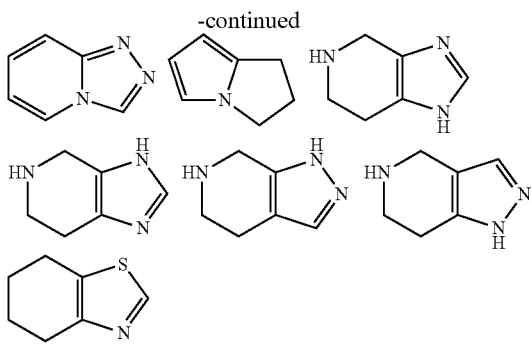

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

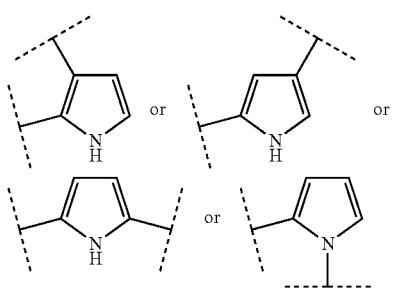

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compound or solvates of a salt of the compound.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-(dimethylamino)-ethanol, 2-aminoethanol, ethylenediamine, N-ethyl-glucamine, hydrabamine, 1H-imidazole, lysine (L-lysine), proline (L-proline), magnesium hydroxide, 4-(2-hydroxyethyl)-morpholine, morpholine, piperazine, potassium hydroxide, 1-(2-hydroxyethyl)-pyrrolidine, 1-(2-hydroxyethyl)-pyrrolidone, sodium hydroxide, triethanolamine (2,2',2''-nitrilotris(ethanol), tromethamine, zinc hydroxide, acetic acid, 2,2-dichloro acetic acid, adipic acid, alginic acid, ascorbic acid (L), L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid (capric acid), dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid (caproic acid), hippuric acid, hydrobromic acid, hydrochloric acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid (caprylic acid), oleic acid, orotic acid, oxalic acid, palmitic acid, pamoic acid (embonic acid), phosphoric acid, propionic acid, (−)-L-pyroglutamic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid and undecylenic acid.

The salts include acetates, ascorbates, benzenesulfonates, benzoates, besylates, bicarbonates, bitartrates, bromides/hydrobromides, Ca-edetates/edetates, camsylates, carbonates, camphorsulfonate, chlorides/hydrochlorides, chlorotheophyllinate, citrates, edisylates, ethane disulfonates, estolates esylates, fumarates, gluceptates, gluconates, glucuronate, glutamates, glycolates, glycollylarsnilates, hexylresorcinates, hippurate, hydrabamines, hydroxymaleates, hydroxynaphthoates, iodides, isethionates, isothionates, lactates, lactobionates, laurylsulfates, malates, maleates, mandelates, methanesulfonates, mesylates, methylbromides, methylnitrates, methylsulfates, mucates, naphthoate, napsylates, nitrates, octadecanoates, oleates, oxalates, pamoates, pantothenates, phenylacetates, phosphates/diphosphates, polygalacturonates, propionates, salicylates, stearates subacetates, succinates, sulfamides, sulfates, sulfosalicylates, tannates, tartrates, teoclates, toluenesulfonates, triethiodides, trifluoroacetates, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

The present invention also includes the co-crystals of any compound according to the invention, i.e. those crystalline forms composed of at least two components (one being the compound according to the invention, the other being co-crystal formers) forming a unique crystalline structure without, in contrast to the crystalline salts, proton transfer from one component to the other. Potential co-crystal formers are acids and bases as listed above for salts/salt formers.

In a representation such as for example

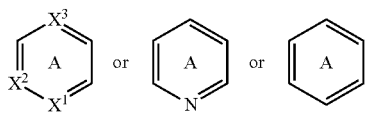

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

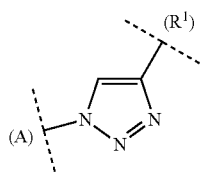

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| Et$_2$O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf (R$_f$) | retention factor |
| RP | reversed phase |

-continued

| | |
|---|---|
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18 OBD, 10 µm, 30×100 mm Part. No. 186003971; X-Bridge C18 OBD, 10 µm, 30×100 mm Part. No. 186003930). The compounds are eluted using different gradients of $H_2O$/ACN wherein 0.2% HCOOH is added to the water (acid conditions). For chromatography under basic conditions the water is made basic according to the following recipe: 5 mL of ammonium hydrogen carbonate solution (158 g to 1 L $H_2O$) and 2 ml 32% ammonia$_{(aq)}$ are made up to 1 L with $H_2O$.

The supercritical fluid chromatography (SFC) of the intermediates and example compounds according to the invention is carried out on a JASCO SFC-system with the following columns: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C2 (250×20 mm, 5 µm).

The analytical HPLC (reaction monitoring) of intermediate compounds is carried out with columns made by Waters and Phenomenex. The analytical equipment is also provided with a mass detector in each case.

HPLC Mass Spectroscopy/UV Spectrometry

The retention times/MS-ESI$^+$ for characterizing the example compounds according to the invention are produced using an HPLC-MS apparatus (high performance liquid chromatography with mass detector) made by Agilent. Compounds that elute at the injection peak are given the retention time $t_{Ret.}$=0.

HPLC-Methods (Preparative)
Prep. HPLC1
HPLC: 333 and 334 Pumps
Column: Waters X-Bridge C18 OBD, 10 µm, 30×100 mm, Part.No. 186003930
Solvent: A: 10 mM $NH_4HCO_3$ in $H_2O$; B: Acetonitrile (HPLC grade)
Detection: UV/Vis-155
Flow: 50 mL/min
Gradient: 0.00-1.50 min: 1.5% B
  1.50-7.50 min: varying
  7.50-9.00 min: 100% B
Prep. HPLC2
HPLC: 333 and 334 Pumps
Column: Waters Sunfire C18 OBD, 10 µm, 30×100 mm, Part. No. 186003971
Solvent: A: $H_2O$+0.2% HCOOH; B: Acetonitrile (HPLC grade)+0.2% HCOOH
Detection: UV/Vis-155
Flow: 50 mL/min
Gradient: 0.00-1.50 min: 1.5% B
  1.50-7.50 min: varying
  7.50-9.00 min: 100% B
HPLC-Methods (Analytic)
LCMSBAS1
HPLC: Agilent 1100 Series
MS: Agilent LC/MSD SL
Column: Phenomenex Mercury Gemini C18, 3 µm, 2×20 mm, Part. No. 00M-4439-B0-CE
Solvent: A: 5 mM $NH_4HCO_3$/20 mM $NH_3$ in $H_2O$; B: Acetonitrile (HPLC grade)
Detection: MS: Positive and negative mode
Mass range: 120-900 m/z
Flow: 1.00 mL/min
Column temperature: 40° C.
Gradient: 0.00-2.50 min: 5%→95% B
  2.50-2.80 min: 95% B
  2.81-3.10 min: 95%→5% B
FECB5
HPLC: Agilent 1100/1200 Series
MS: Agilent LC/MSD SL
Column: Waters X-Bridge C18 OBD, 5 µm, 2.1×50 mm
Solvent: A: 5 mM $NH_4HCO_3$/19 mM $NH_3$ in $H_2O$; B: Acetonitrile (HPLC grade)
Detection: MS: Positive and negative mode
Mass range: 105-1200 m/z
Flow: 1.20 mL/min
Column temperature: 35° C.
Gradient: 0.00-1.25 min: 5%→95% B
  1.25-2.00 min: 95% B
  2.00-2.01 min: 95%→5% B
FECBM3ESI
HPLC: Agilent 1100/1200 Series
MS: Agilent LC/MSD SL
Column: Waters X-Bridge C18 OBD, 5 µm, 2.1×50 mm
Solvent: A: 5 mM $NH_4HCO_3$/19 mM $NH_3$ in $H_2O$; B: Acetonitrile (HPLC grade)
Detection: MS: Multimode ESI Positive and negative mode
Mass range: 105-1200 m/z
Flow: 1.20 mL/min Column temperature: 35° C.
Gradient: 0.00-1.25 min: 5%→100% B
1.25-2.00 min: 100% B
2.00-2.01 min: 100%→5% B
VAB
HPLC: Agilent 1100/1200 Series
MS: Agilent LC/MSD SL
Column: Waters X-Bridge BEH C18, 2.5 µm, 2.1×30 mm XP
Solvent: A: 5 mM $NH_4HCO_3$/19 mM $NH_3$ in $H_2O$; B: Acetonitrile (HPLC grade)
Detection: MS: Positive and negative mode
Mass range: 100-1200 m/z
Flow: 1.40 mL/min
Column temperature: 45° C.
Gradient: 0.00-1.00 min: 5%→100% B
1.00-1.37 min: 100% B
1.37-1.40 min: 100%→5% B
FA-8
HPLC-MS: Waters—Alliance 2996
Column: Symmetryshield C18, 5 µm, 4.6×250 mm
Solvent: A: $H_2O$+0.1% TFA; B: Acetonitrile (HPLC grade)
Detection: MS: Positive and negative mode
Mass range: 100-1200 m/z
Flow: 1.00 mL/min
Column temperature: 25° C.
Gradient: 2.00-8.00 min: 20%→80% B
8.00-19.00 min: 80% B
19.00-20.00 min: 80%→20% B
FSUN2
HPLC: Agilent 1100/1200 Series
MS: Agilent LC/MSD SL
Column: Waters Sunfire C18, 5 µm, 2.1×50 mm
Solvent: A: $H_2O$+0.2% formic acid; B: Acetonitrile (HPLC grade)
Detection: MS: Positive and negative mode
Mass range: 105-1200 m/z
Flow: 1.20 mL/min
Column temperature: 35° C.
Gradient: 0.0 min: 5% B
0.0-1.50 min: 5%→95% B
1.50-2.00 min: 95% B
2.00-2.01 min: 95%→5% B
LCMS A
HPLC-MS: LCMS/MS API 2000 (Applied Biosystem)
Column: Agilent Zorbax Extend C18 4.6×50 mm, 5 micron
Solvent: A: 10 mM $NH_4OAc$ in $H_2O$; B: Acetonitril (HPLC grade)
Detection: MS: Positive and negative mode
Mass range: 100-800 m/z
Flow: 1.20 mL/min
Column temperature: 25° C.
Gradient: 0.0 min: 10% B
0.0-1.50 min: 10%→30% B
1.50-3.00 min: 30%→90% B
3.00-4.00 min: 90% B
4.00-5.00 min: 90%→10% B
LCMS B
HPLC-MS: Alliance HT Waters ZQ Mass (Waters)
Column: Agilent Zorbax Extend C18 4.6×50 mm, 5 micron
Solvent: A: 10 mM $NH_4OAc$ in $H_2O$; B: Acetonitrile (HPLC grade)
Detection: MS: Positive and negative mode
Mass range: 100-800 m/z
Flow: 1.20 mL/min
Column temperature: 50° C.
Gradient: 0.01 min: 5% B
0.01-0.75 min: 5% B
0.75-1.50 min: 5%→15% B
1.50-3.00 min: 15% B→90% B
3.00-4.00 min: 90% B
4.00-5.00 min: 90% B→5% B The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods or methods described herein. Substances described in the literature are prepared according or in analogy to the published methods of synthesis.

General Reaction Scheme and Summary of the Synthesis Route

Compounds (I) according to the invention can be synthesized using a SUZUKI reaction (*J. Org. Chem.*, 2007, 72, 4067-4072; *Org. Lett.*, 2011, 13, 252-255; *J. Org. Chem.*, 2004, 69, 7779-7782) either starting from A-1 and B-1 or A-2 and B-2 or C-1 and D-1 or C-2 and D-2 (scheme 1). Additional derivatization steps, e.g. at position $R^5$ and/or A, like e.g. ester cleavage, amide coupling, SUZUKI reactions or reduction of an acid derivative to the corresponding amine or alcohol (not depicted in scheme 1) can be included.

Scheme 1:

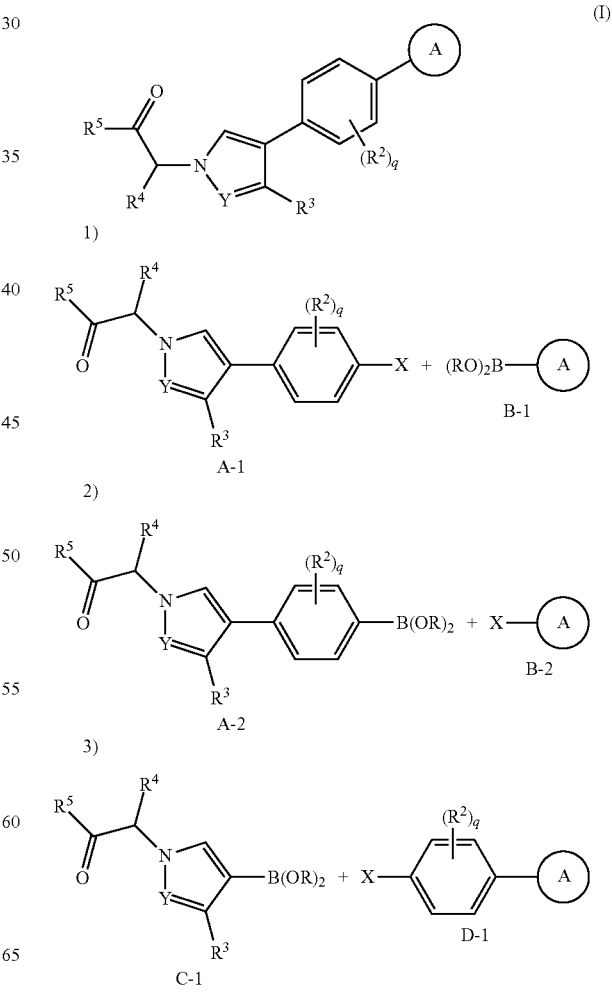

4)

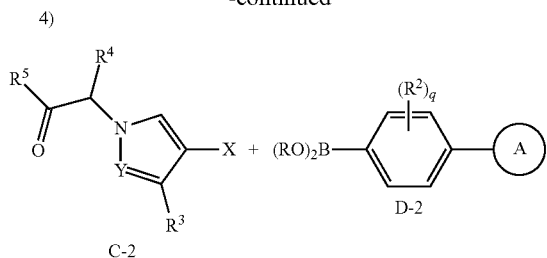

in all schemes:
X = leaving group, (e.g. halogen, triflate, mesylate, tosylate) preferably Cl, Br, I;
B(OR)$_2$ = boronic acid or boronic acid derivative, e.g. cyclic boronic acid esters but also BF$_3^-$M$^+$ optional derivatization steps, especially in A and R$^5$, are possible in steps 1) to 4)

Synthesis of boronic acid derivatives A-2 and halides A-1 are shown in scheme 2 or are commercially available. The bicyclic heteroaryls B-1, B-2, D-1 and D-2 are synthesized as shown in scheme 3 and 4 or are commercially available. The compounds C-1 and C-2 are commercially available.

The boronic acid derivative A-2 can be synthesized either via a MIYAURA borylation reaction (*J. Org. Chem.*, 1995, 60, 7508-7510; *J. Org. Chem.*, 2012, 77, 8678-8688) starting from halide A-1 or using an aniline E-6 as starting material and applying a SANDMEYER borylation reaction (*Angewandte Chemie* (Int. Ed.), 2010, 49(10), 1846-1849; *J. Org. Chem.*, 2013, 78(5), 1923-1933). Halide A-1 is prepared either from the aniline E-6 using a SANDMEYER reaction (*Synthesis*, 2007, 2534-2538; *J. Am. Chem. Soc.*, 1957, 79(11): 2942-2948) or from intermediate E-7 via a SUZUKI reaction (→E-8) followed by an alkylation reaction. SUZUKI reaction of either E-1 and C-1 or E-1 and E-2 followed by an alkylation reaction with E-4 deliver the nitro-derivative E-5, which can be reduced under hydrogen atmosphere in the presence of palladium on carbon or RANEY nickel to the aniline E-6. Furthermore the aniline E-6 can also synthesized from E-9 and C-2 by applying a SUZUKI reaction.

Scheme 2:

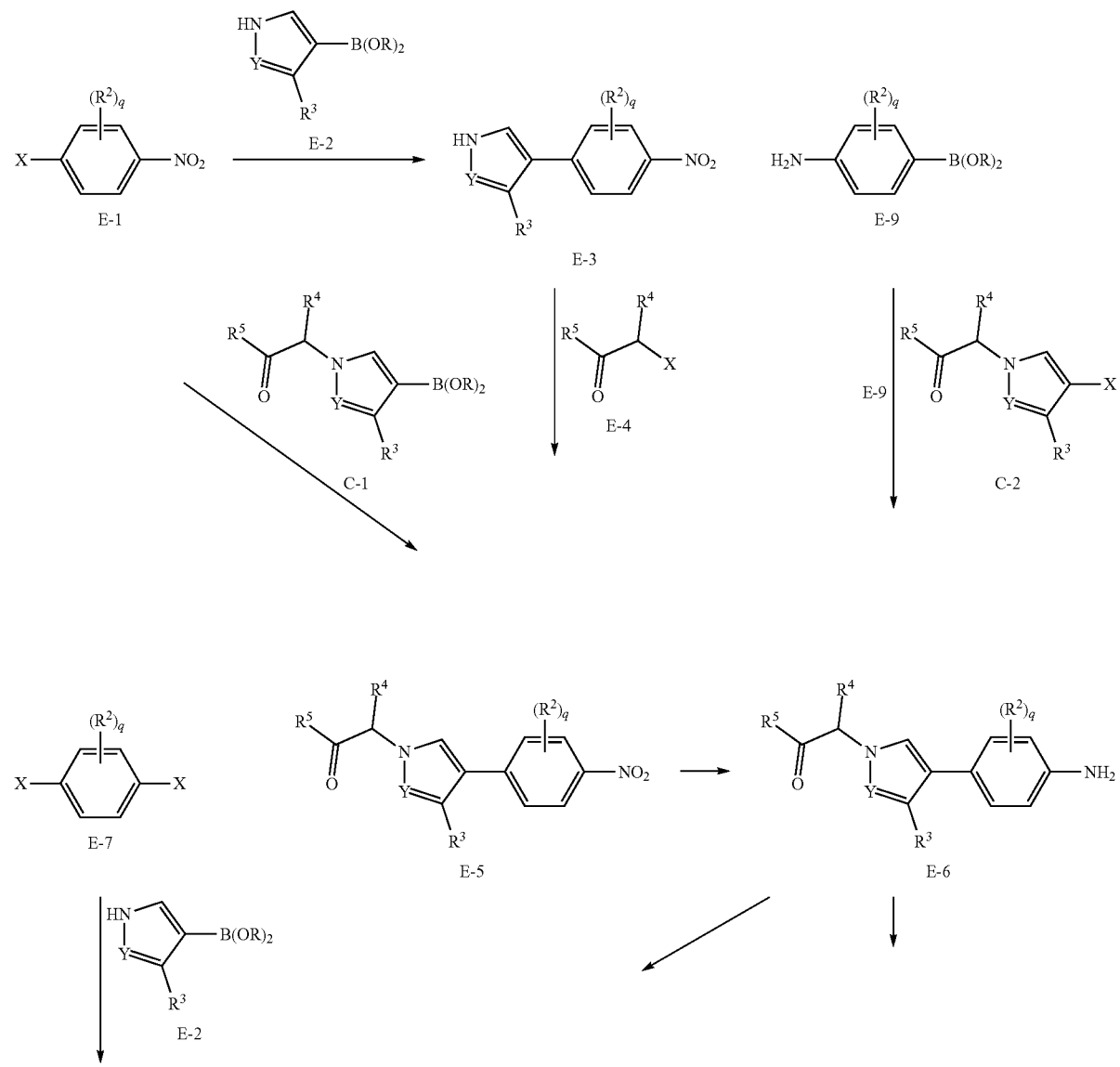

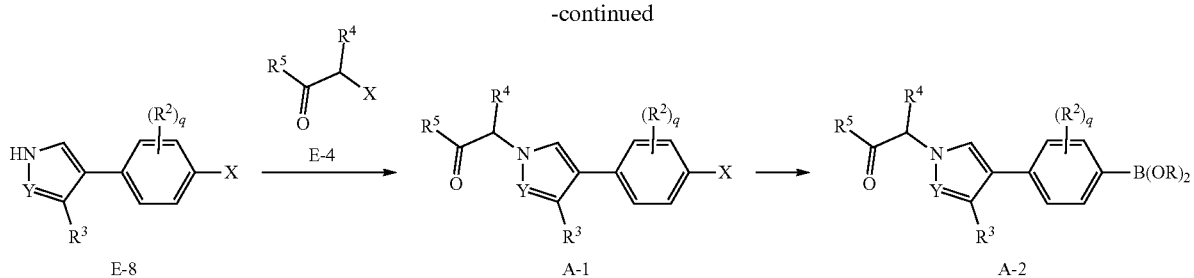

The boronic acid derivatives $B^{A1}$-1 and $B^{A2}$-1 (scheme 3) can be synthesized via a MIYAURA borylation reaction (*J. Org. Chem.*, 1995, 60, 7508-7510; *J. Org. Chem.*, 2012, 77, 8678-8688) starting from halides $B^{A1}$-2 and $B^{A2}$-2. Halides $B^{A1}$-2 and $B^{A2}$-2 are commercially available or can be synthesized as described below:

Halide $B^{A1}$-2 can be synthesized applying a cyclization reaction using F-4. F-4 can be synthesized starting from F-1 and performing a condensation reaction with methoxyamine (→F-2) followed by a SUZUKI reaction with F-3.

Starting from an isoquinoline (F-5), a halogen can be introduced at position 4 via an electrophilic aromatic substitution reaction leading to halide $B^{A2}$-2. Modifications of the residue at position 6 of $B^{A2}$-2 are possible (e.g. reduction of an acid derivative to the corresponding amine or alcohol).

Scheme 3:

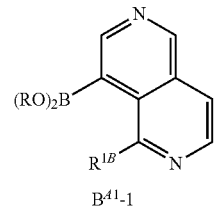

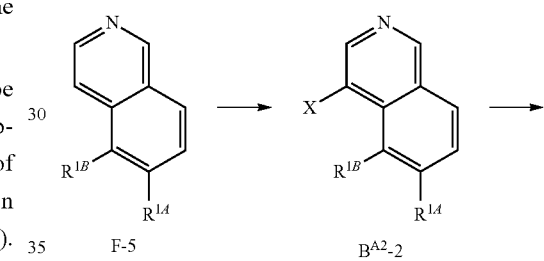

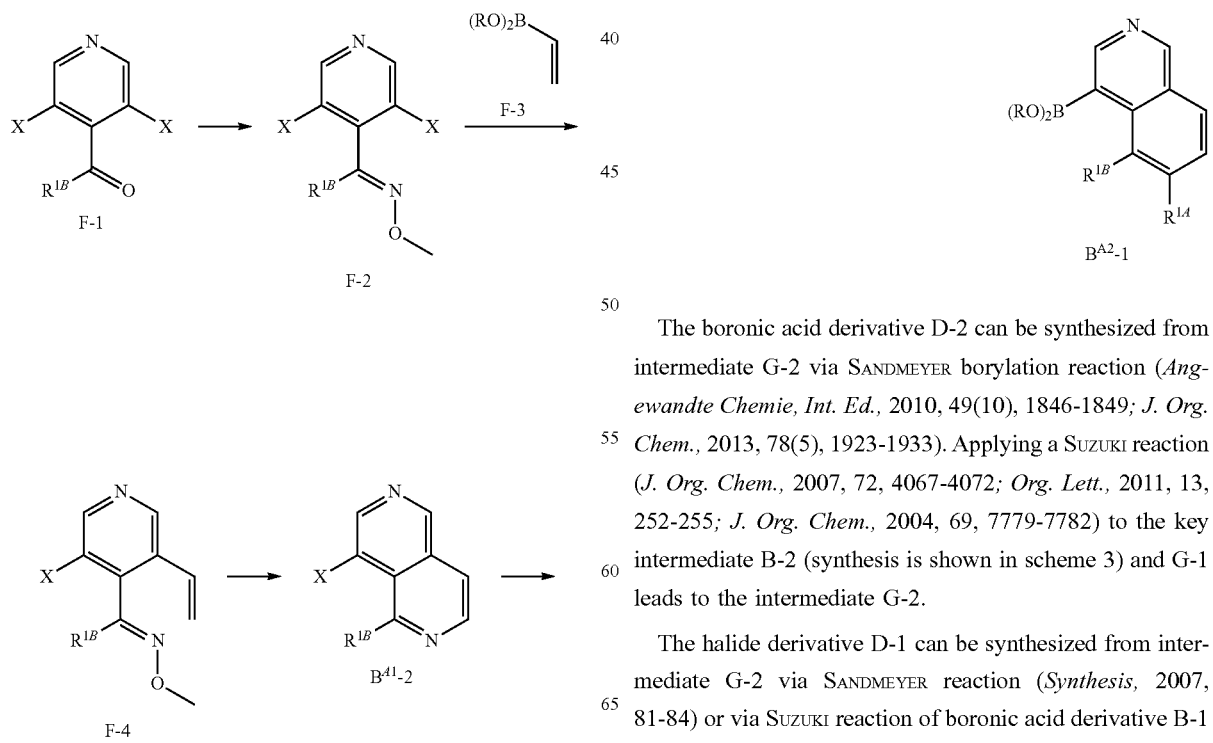

The boronic acid derivative D-2 can be synthesized from intermediate G-2 via SANDMEYER borylation reaction (*Angewandte Chemie, Int. Ed.*, 2010, 49(10), 1846-1849; *J. Org. Chem.*, 2013, 78(5), 1923-1933). Applying a SUZUKI reaction (*J. Org. Chem.*, 2007, 72, 4067-4072; *Org. Lett.*, 2011, 13, 252-255; *J. Org. Chem.*, 2004, 69, 7779-7782) to the key intermediate B-2 (synthesis is shown in scheme 3) and G-1 leads to the intermediate G-2.

The halide derivative D-1 can be synthesized from intermediate G-2 via SANDMEYER reaction (*Synthesis*, 2007, 81-84) or via SUZUKI reaction of boronic acid derivative B-1 an dihalide E-7.

Scheme 4:

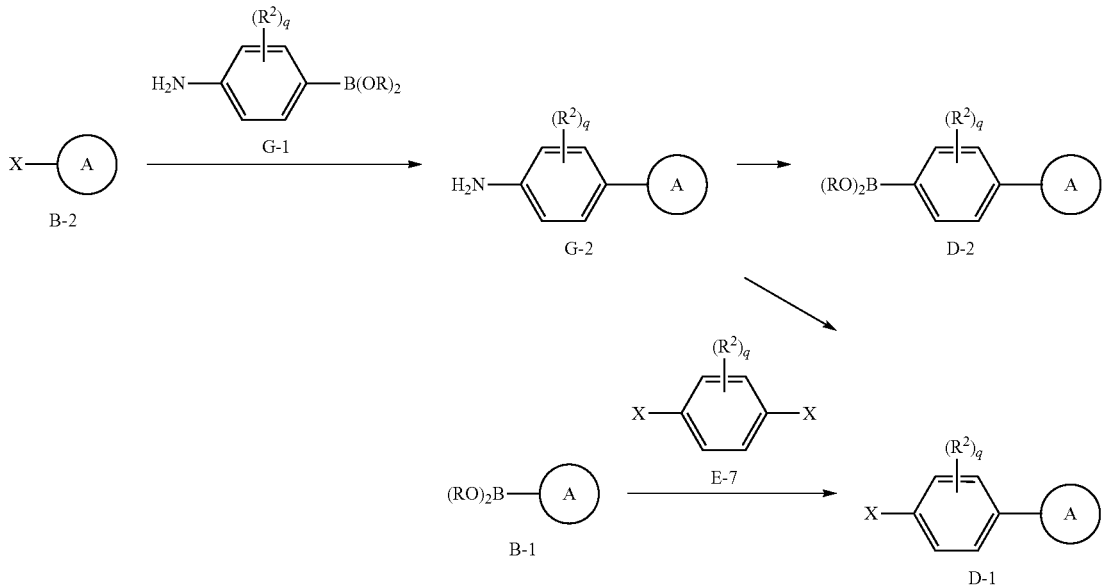

Synthesis of Intermediates A-1 and A-2

Synthesis of Intermediates A-1a and A-2a

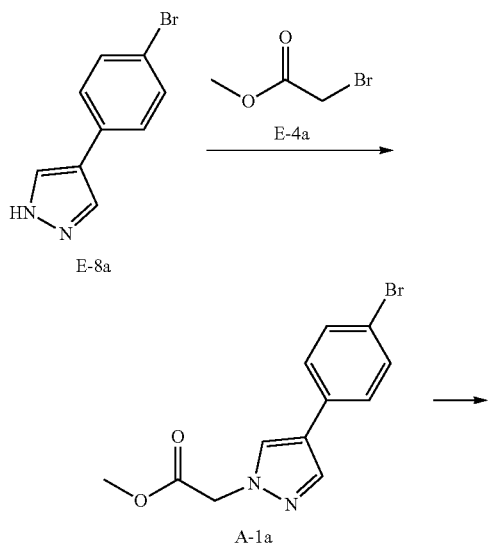

4-(4-Bromo-phenyl)-1H-pyrazole E-8a (1.00 g; 4.39 mmol) is dissolved in DMF (15 mL) and sodium hydride (150 mg; 5.94 mmol) is added. The reaction mixture is stirred for 30 min and then bromo-acetic acid methyl ester E-4a (500 µL; 5.39 mmol) is added at 25° C. After 18 h, the reaction mixture is quenched with aqueous NH$_4$Cl solution and extracted with DCM twice. The organic phase is dried over MgSO$_4$ and the solvent is evaporated. The crude product is purified using normal phase chromatography (DCM/MeOH: 100:0→90:10) to afford the desired intermediate A-1a.

Yield: 72% (955 mg; 3.17 mmol)

HPLC-MS: (M+H)$^+$=295/297; t$_{Ret}$=0.91 min; method VAB

Bis(pinacolato)biboron (710 mg; 2.80 mmol) and KOAc (1.37 g; 13.97 mmol) are added to a stirring solution of A-1a (550 mg; 1.86 mmol) in dioxane (20 mL) and degassed with argon for 20 min. [1,1'-Bis[diphenylphosphino]ferrocene] dichloropalladium[0] dichloromethane (61 mg; 0.075 mmol) is added then. The reaction mixture is heated at 100° C. for 18 h. The reaction mixture is diluted with NaHCO$_3$ solution and then extracted with DCM twice. The organic phase is dried over MgSO$_4$ and the solvent is evaporated. The crude product is purified using normal phase chromatography (cyclohexan/EtOAc: 85:15) to afford the desired intermediate A-2a.

Yield: 89% (570 mg; 1.66 mmol)

HPLC-MS: (M+H)$^+$=343; t$_{Ret}$=0.97 min; method VAB

Synthesis of Intermediates A-1b, A-1c and A-2b

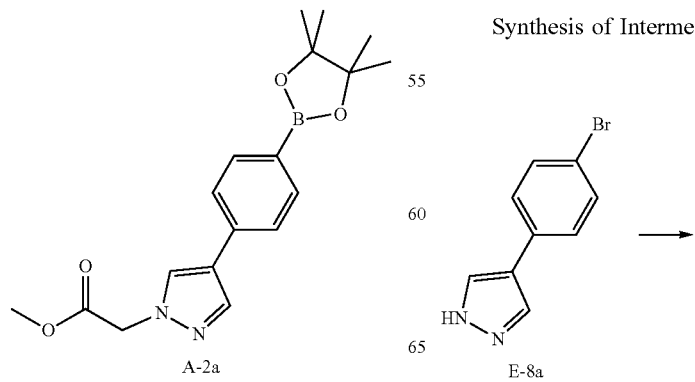

-continued

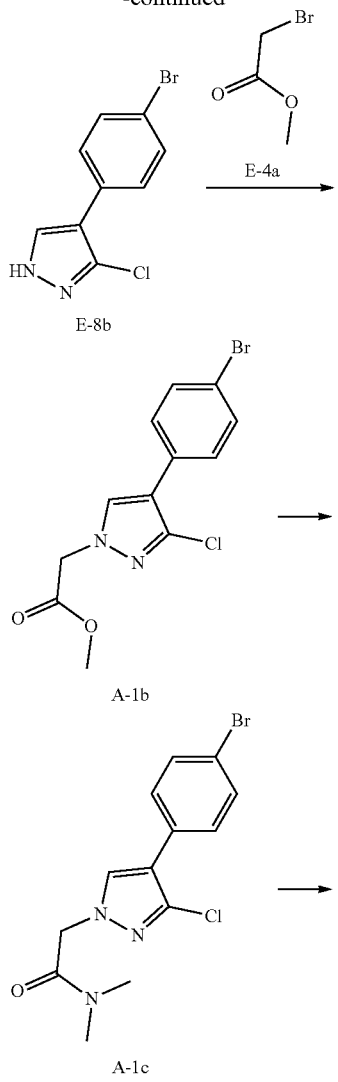

product is purified using normal phase chromatography (cyclohexan/EtOAc: 80:20) to afford the desired intermediate E-8b.

Yield: 69% (2.80 g; 10.89 mmol)

HPLC-MS: (M+H)$^+$=257/259; method LCMS A

Intermediate E-8b (1.90 g; 7.39 mmol) is dissolved in ACN (150 mL) and potassium carbonate (2.54 g; 18.41 mmol) is added. The reaction mixture is stirred for 30 min and then bromo-acetic acid methyl ester E-4a (1.24 g; 8.16 mmol) is added at 25° C. After 18 h the reaction mixture is quenched with aqueous NH$_4$Cl solution and extracted with DCM twice. The organic phase is dried over MgSO$_4$ and the solvent is evaporated. The crude product is purified using normal phase chromatography (DCM/MeOH: 100:0→90:10) to afford the desired intermediate A-1b.

Yield: 62% (1.50 g; 4.56 mmol)

HPLC-MS: (M+H)$^+$=329/331; method LCMS A

Intermediate A-1b (500 mg; 1.52 mmol) is dissolved in a 2 M solution of dimethylamine in THF (5 mL; 10 mmol) and heated in a microwave reactor to 140° C. for 4 h. The reaction mixture is cooled to 25° C., HATU (865 mg; 2.28 mmol) is added and the mixture is stirred for 2 h at 25° C. The solvents are evaporated and the crude product is purified using reversed phase chromatography (method: prep. HPLC1) to afford the desired intermediate A-1c.

Yield: 77% (400 mg; 1.17 mmol)

HPLC-MS: (M+H)$^+$=344/346; $t_{Ret}$=0.92 min; method VAB

Bis(pinacolato)biboron (505 mg; 1.95 mmol) and KOAc (865 mg; 8.73 mmol) are added to a stirring solution of intermediate A-1c (400 mg; 1.17 mmol) in dioxane (10 mL) and degassed with argon for 20 min. [1,1'-Bis[diphenylphosphino]ferrocene]dichloropalladium[0] dichloromethane (51 mg; 0.059 mmol) is added then. The reaction mixture is heated at 95° C. for 2 h. The reaction mixture is diluted with NaHCO$_3$ solution and then extracted with DCM twice. The organic phase is dried over MgSO$_4$ and the solvent is evaporated. The crude product is purified using normal phase chromatography (solvent EtOAc) to afford the desired intermediate A-2b.

Yield: 93% (424 mg; 1.09 mmol)

HPLC-MS: (M+H)$^+$=390/392; $t_{Ret}$=0.98 min; method VAB

Synthesis of Intermediate A-2c

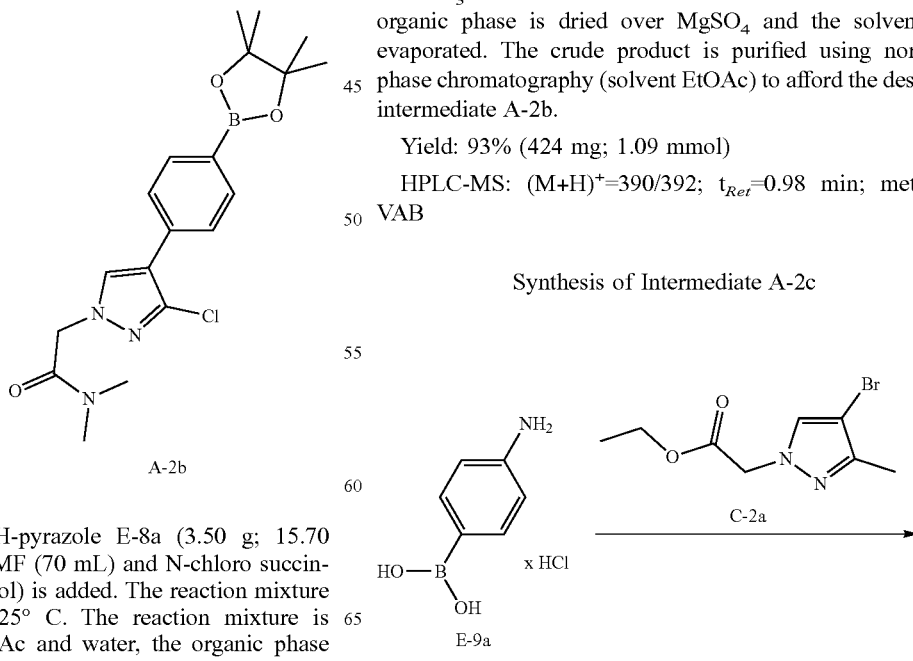

4-(4-Bromo-phenyl)-1H-pyrazole E-8a (3.50 g; 15.70 mmol) is dissolved in DMF (70 mL) and N-chloro succinimide (2.50 g; 18.80 mmol) is added. The reaction mixture is stirred for 18 h at 25° C. The reaction mixture is partitioned between EtOAc and water, the organic phase dried over MgSO$_4$ and the solvent is evaporated. The crude

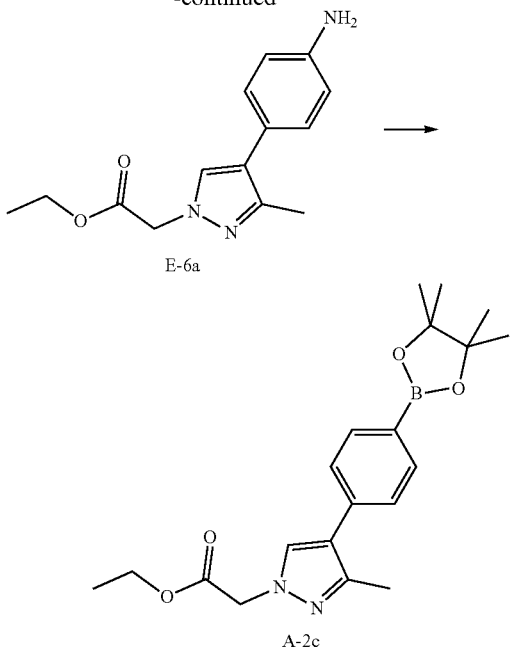

Halide C-2a (5.00 g; 20.24 mmol), (4-aminophenyl)boronic acid hydrochloride E-9a (5.26 g; 30.35 mmol) and caesium carbonate (75 mg; 0.23 mmol) are suspended in a mixture of dioxane (75 mL) and water (15 mL). The reaction mixture is purged with argon, Pd(OAc)$_2$ (227 mg; 1.01 mmol) and 2-dicyclohexylphosphino-2',6'-dimethoxybiphenyl (831 mg; 2.02 mmol) are added and the mixture is stirred for 16 h at 80° C. The reaction mixture is diluted with water and then extracted with EtOAc twice. The organic phase is dried over MgSO$_4$ and the solvent is evaporated. The crude product is purified using normal phase chromatography to afford the desired intermediate E-6a.

Yield: 65% (3.40 g; 13.11 mmol)

HPLC-MS: (M+H)$^+$=260; $t_{Ret}$=2.50 min; method LCMS A

Bis(pinacolato)biboron (734 mg; 2.89 mmol) and tert-butyl nitrite (398 mg; 3.86 mmol) are added at 25° C. to a stirring solution of intermediate E-6a (500 mg; 1.93 mmol) in ACN (12 mL) under nitrogen atmosphere. The reaction mixture is heated at 80° C. for 12 h. The reaction mixture is diluted with NaHCO$_3$ solution and then extracted with DCM twice. The organic phase is dried over MgSO$_4$ and the solvent is evaporated. The crude product is purified using normal phase chromatography (cyclohexan/EtOAc: 95:5-80:20) to afford the desired intermediate A-2c.

Yield: 49% (350 mg; 0.95 mmol)

HPLC-MS: (M+H)$^+$=371; $t_{Ret}$=3.60 min; method LCMS A

The following intermediates A-2 are synthesized analogously to A-2a to A-2c. The starting materials are commercially available.

TABLE 1

| # | structure | MS (M + H)$^+$; $t_{Ret}$ HPLC [min] | HPLC-MS method |
|---|---|---|---|
| A-2a | 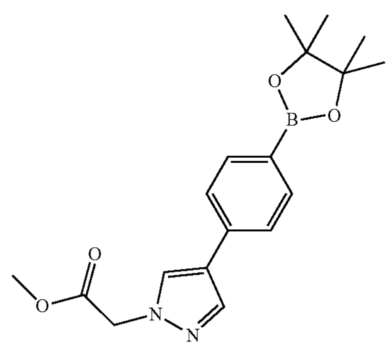 | M + H = 343; $t_{Ret}$ = 0.97 | VAB |
| A-2b | 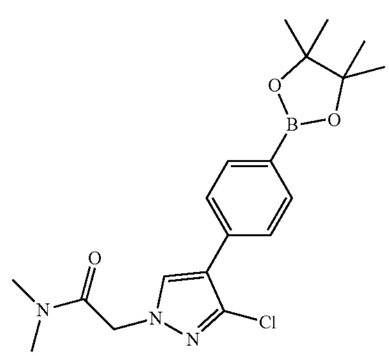 | M + H = 390/392; $t_{Ret}$ = 0.98 | VAB |

TABLE 1-continued

| # | structure | MS (M + H)+; $t_{Ret}$ HPLC [min] | HPLC-MS method |
|---|---|---|---|
| A-2c | 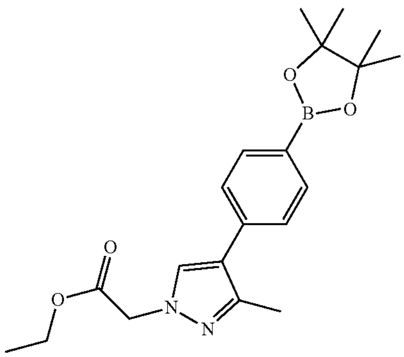 [SMILES: CCOC(=O)Cn1cc(-c2ccc(B3OC(C)(C)C(C)(C)O3)cc2)c(C)n1] | M + H = 371; $t_{Ret}$ = 3.60 | LCMS A |
| A-2d | 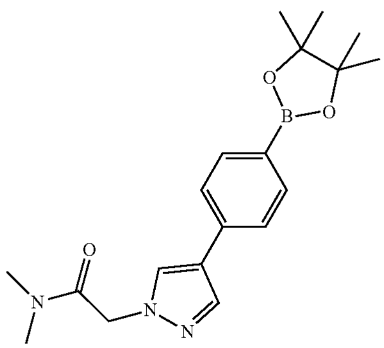 | M + H = 356; $t_{Ret}$ = 0.90 | VAB |
| A-2e | 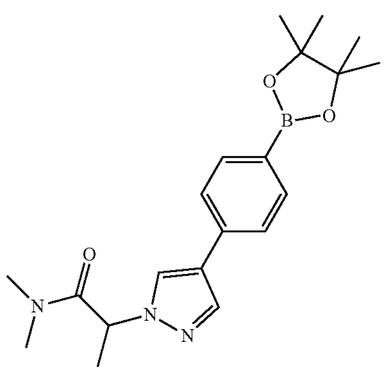 | M + H = 357; | LCMS A |
| A-2f | 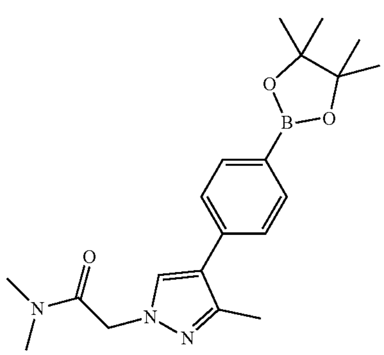 | M + H = 371; | LCMS A |

TABLE 1-continued

| # | structure | MS (M + H)+; $t_{Ret}$ HPLC [min] | HPLC-MS method |
|---|---|---|---|
| A-2g | 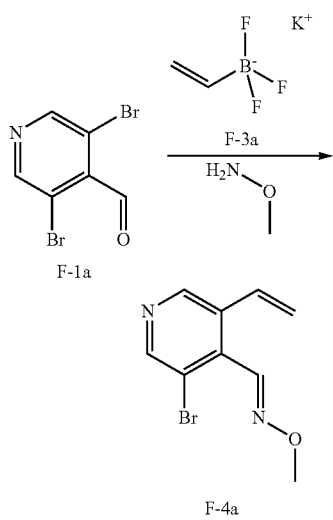 | M + H = 361; | LCMS A |

Synthesis of Intermediates B-2

Synthesis of Intermediate $B^{41}$-2a

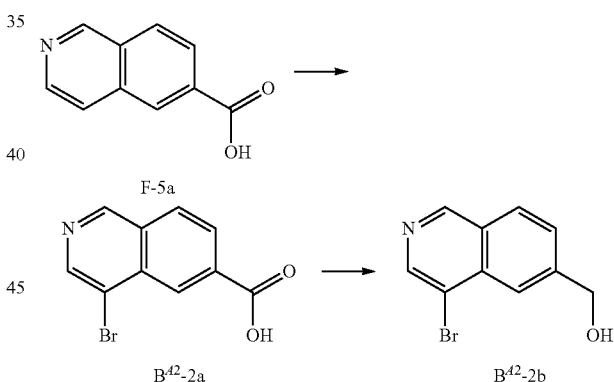

3,5-Dibromo-pyridine-4-carbaldehyde F-1a (5.00 g; 18.31 mmol), potassium vinyltrifluoroborate F-3a (2.55 g; 18.09 mmol) and caesium carbonate (12.00 g; 36.09 mmol) are suspended in a mixture of 1,2-dimethoxyethane (75 mL) and water (25 mL). The reaction mixture is purged with argon, [1,1'-bis[diphenylphosphino]-ferrocene]dichloropalladium[0] dichloromethane (150 mg; 0.18 mmol) is added and the mixture is stirred for 30 h at 25° C. To this reaction mixture O-methyl-hydroxylamine hydrochloride (6.90 g; 81.00 mmol) is added and the mixture is stirred at 40° C. for 5 h. The solvents are evaporated and the crude product is suspended in an aqueous potassium carbonate solution and extracted three times with DCM. The organic layer is separated, dried over MgSO$_4$ and the solvent is evaporated. The crude product is purified using normal phase chromatography (DCM/MeOH) to afford the desired intermediate F-4a.

Yield: 36% (1.60 g; 6.64 mmol)

HPLC-MS: (M+H)+=241/243; $t_{Ret}$=0.91 min; method VAB Intermediate F-4a (1.60 g; 6.64 mmol) is dissolved in diphenyl ether (10 mL) and stirred for 2 h at 200° C. The reaction mixture is diluted with DCM and subjected to an ion exchange column (SCX-2; Macherey Nagel). The column is washed with DCM and MeOH. Afterwards the crude compound is eluated with ammonia dissolved in MeOH. The solvents are evaporated and the crude product $B^{41}$-2a is purified using reversed phase chromatography (Method: prep. HPLC1).

Yield: 50% (676 mg; 3.24 mmol)

HPLC-MS: (M+H)+=209/211; $t_{Ret}$=0.66 min; method VAB

Synthesis of Intermediates $B^{42}$-2a and $B^{42}$-2b

Isoquinoline-6-carboxylic acid F-5a (9.00 g; 52.02 mmol) and N-bromosuccinimide (NBS) (11.10 g; 62.36 mmol) are suspended in AcOH (270 mL) and the reaction mixture is stirred for 4 h at 90° C. The reaction mixture is cooled down to 20° C., the solid material is filtered off, washed with water and with MeOH. The remaining solid material is dried in vacuum affording the desired intermediate $B^{42}$-2a.

Yield: 69% (9.00 g; 35.71 mmol)

HPLC-MS: (M+H)+=252/254; $t_{Ret}$=0.77 min; method VAS

Intermediate $B^{42}$-2a (2.50 g; 9.92 mmol) is dissolved in THF (60 mL). 1,1'-carbonyldiimida-zole (1.77 g; 10.93 mmol) is added to the solution and the mixture is stirred for 1 h at 60° C. Afterwards the mixture is cooled down to 0° C. and is added to a solution of sodium borohydride (1.13 g; 29.89 mmol) dissolved in water (45 mL). The reaction mixture is stirred for 2 h, then diluted with water and extracted twice with DCM. The organic phase is dried over MgSO$_4$ and the solvent is evaporated. The crude product is purified using normal phase chromatography to afford the desired intermediate B$^{42}$-2b.

Yield: 64% (1.50 g; 6.30 mmol)

HPLC-MS: (M+H)$^+$=238/240; t$_{Ret}$=2.68 min; method LCMS A

The following intermediates B-2 can be synthesized in analogy to the procedures as described above with commercially available starting materials or are commercially available as such.

TABLE 2

| # | structure | MS (M + H)$^+$; t$_{Ret}$ HPLC [min] | HPLC-MS method |
|---|---|---|---|
| B$^{41}$-2a | 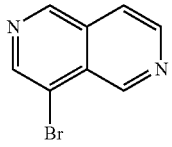 | M + H = 209/211; t$_{Ret}$ = 0.66 | VAB |
| B$^{42}$-2a | 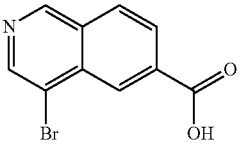 [SMILES: O=C(O)c1ccc2cncc(Br)c2c1] | M + H = 252/254; t$_{Ret}$ = 0.77 | VAS |
| B$^{42}$-2b | 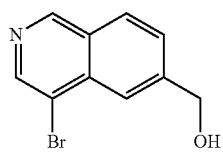 [SMILES: OCc1ccc2cncc(Br)c2c1] | M + H = 238/240; t$_{Ret}$ = 2.68 | LCMS A |
| B$^{42}$-2c | 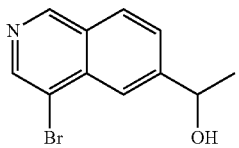 | M + H = 252/254 | LCMS A |
| B$^{42}$-2d | 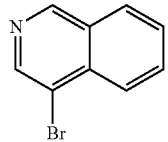 [SMILES: Brc1cncc2ccccc12] | commercially available | — |

Synthesis of Intermediates D-1

Synthesis of Intermediate D$^{42}$-1a

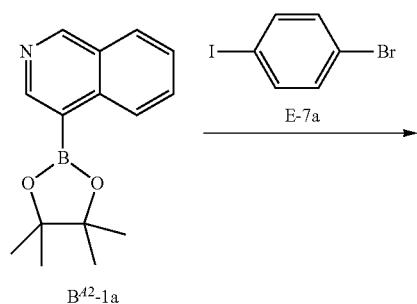

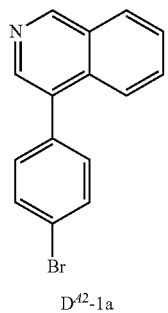

B$^{42}$-1a (234 mg; 0.88 mmol), 1-bromo-4-iodobenzene E-7a (250 mg; 0.88 mmol) and caesium carbonate (1727 mg; 3.71 mmol) are suspended in a mixture of THF (2.5 mL) and water (0.5 mL). The reaction mixture is purged with argon, [1,1'-bis[diphenylphosphino]-ferrocene]dichloropalladium [0] dichloromethane (73 mg; 0.09 mmol) is added and the mixture is stirred for 4 d at 25° C. The solvent is evaporated and the crude product is purified using reversed phase chromatography (method: prep. HPLC1) to afford the desired intermediate D$^{42}$-1a.

Yield: 74% (185 mg; 0.65 mmol)

HPLC-MS: (M+H)$^+$=284/286; t$_{Ret}$=1.04 min; method VAB

Preparation of Compounds of Formula (I) According to the Invention

Synthesis of I-001 and I-002

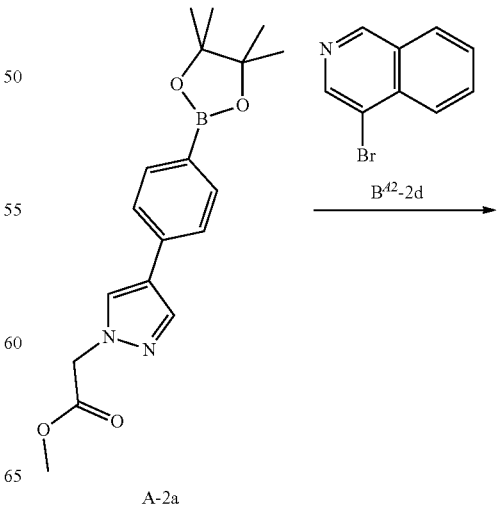

Synthesis of I-003

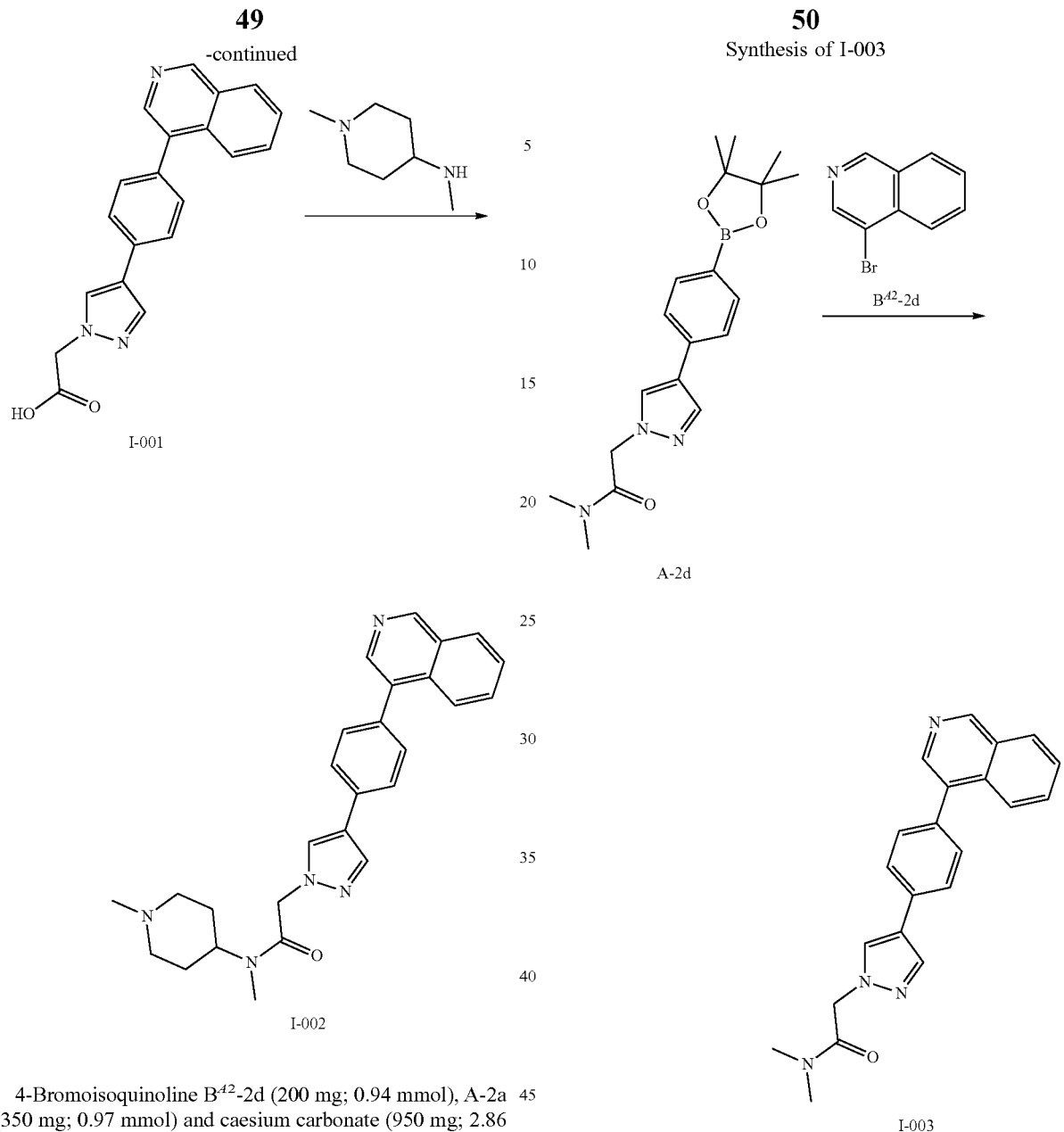

4-Bromoisoquinoline B^42-2d (200 mg; 0.94 mmol), A-2a (350 mg; 0.97 mmol) and caesium carbonate (950 mg; 2.86 mmol) are suspended in a mixture of 1,2-dimethoxyethane (12 mL) and water (4 mL). The reaction mixture is purged with argon, [1,1'-bis[diphenylphosphino]ferrocene]dichloropalladium[0] dichloromethane (40 mg; 0.048 mmol) is added and stirred for 60 min in a micro wave reactor at 105° C. The solvents are evaporated and the crude product I-001 is suspended in a mixture of water and DCM. The water layer is separated and the pH value is adjusted with hydrochloric acid to be below pH 1. The solid material is filtered off, washed with water and dried in vacuum.

I-001 (110 mg; 0.33 mmol) is dissolved in DCM (3 mL) and N,N-diisopropyl-N-ethylamine (165 µL; 1.00 mmol), HATU (143 mg; 0.37 mmol) and 1-methyl-4-(methylamino)piperidine (45 mg; 0.35 mmol) are added. The reaction mixture is stirred at 20° C. for 16 h. The solvents are evaporated and the crude product I-002 is purified using reversed phase chromatography (method: prep. HPLC1).

Yield: 30% (122 mg; 0.28 mmol)

HPLC-MS: $(M+H)^+$=440; $t_{Ret}$=1.08 min; method LCMS-BAS1

4-Bromoisoquinoline $B^{42}$-2d (15 mg; 0.07 mmol), A-2d (30 mg; 0.08 mmol) and caesium carbonate (75 mg; 0.23 mmol) are suspended in a mixture of 1,2-dimethoxyethane (3 mL) and water (1 mL). The reaction mixture is purged with argon, [1,1'-bis[diphenylphosphino]ferrocene]dichloropalladium[0] dichloromethane (5 mg; 0.006 mmol) is added and stirred for 30 min in a micro wave reactor at 90° C. The solvents are evaporated and the crude product I-003 is purified using reversed phase chromatography (method: prep. HPLC1).

Yield: 57% (14 mg; 0.04 mmol)

HPLC-MS: $(M+H)^+$=357; $t_{Ret}$=1.03 min; method LCMS-BAS1

The following compounds (I) according to the invention can be synthesized in analogy to the procedures as described above with commercially available starting materials or intermediates prepared as herein described.

TABLE 3

| # | structure | MS (M + H)+; $t_{Ret}$ HPLC [min] | HPLC-MS method | IC$_{50}$ CDK8 [nM] |
|---|---|---|---|---|
| I-001 | 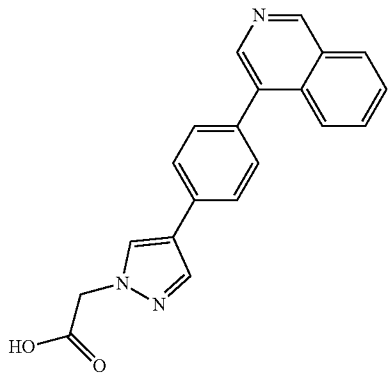 [SMILES: O=C(O)Cn1cc(-c2ccc(-c3cncc4ccccc34)cc2)cn1] | M + H = 330; $t_{Ret}$ = 0.68 | VAB | — |
| I-002 | 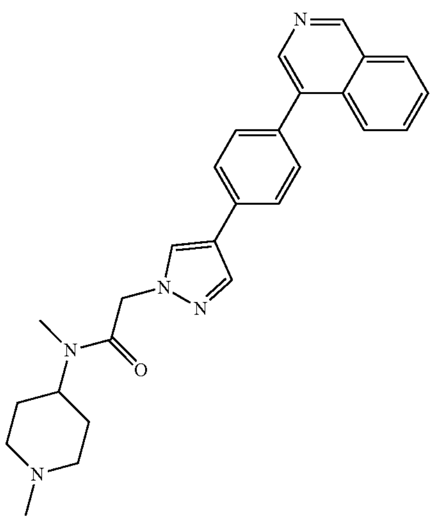 [SMILES: CN1CCC(N(C)C(=O)Cn2cc(-c3ccc(-c4cncc5ccccc45)cc3)cn2)CC1] | M + H = 440; $t_{Ret}$ = 1.08 | LCMSBAS1 | 1.5 |
| I-003 | 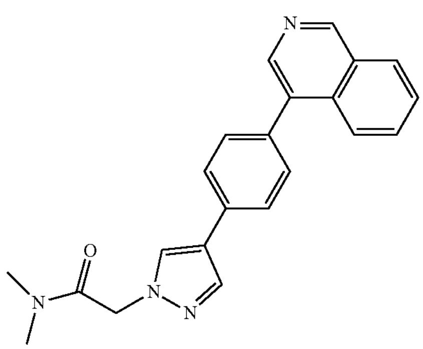 [SMILES: CN(C)C(=O)Cn1cc(-c2ccc(-c3cncc4ccccc34)cc2)cn1] | M + H = 357; $t_{Ret}$ = 1.03 | LCMSBAS1 | 1.1 |
| I-004 | 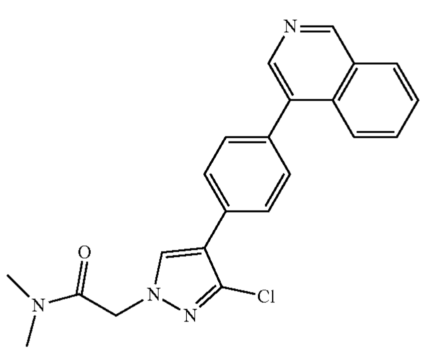 [SMILES: CN(C)C(=O)Cn1cc(-c2ccc(-c3cncc4ccccc34)cc2)c(Cl)n1] | M + H = 391; $t_{Ret}$ = 1.19 | LCMSBAS1 | 1.8 |

TABLE 3-continued

| # | structure | MS (M + H)+; $t_{Ret}$ HPLC [min] | HPLC-MS method | IC$_{50}$ CDK8 [nM] |
|---|---|---|---|---|
| I-005 | Absolute | M + H = 371; $t_{Ret}$ = 1.10 | LCMSBAS1 | 1.0 |
| I-006 | Absolute | M + H = 371; $t_{Ret}$ = 1.09 | LCMSBAS1 | 2.5 |
| I-007 | 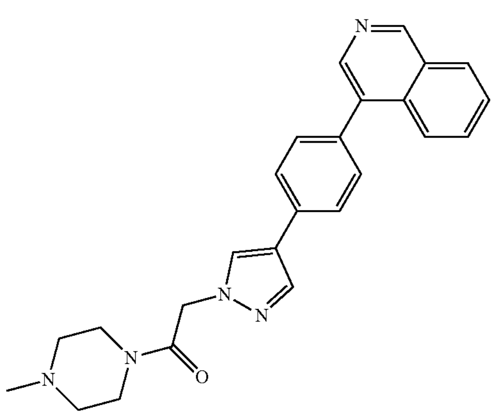 [SMILES: CN1CCN(C(=O)Cn2cc(-c3ccc(-c4cncc5ccccc45)cc3)cn2)CC1] | M + H = 412; $t_{Ret}$ = 1.03 | LCMSBAS1 | 1.2 |

TABLE 3-continued

| # | structure | MS (M + H)+; $t_{Ret}$ HPLC [min] | HPLC-MS method | IC$_{50}$ CDK8 [nM] |
|---|---|---|---|---|
| I-008 | 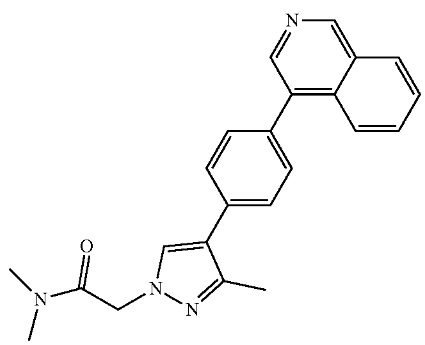 [SMILES: Cc1nn(CC(=O)N(C)C)cc1-c1ccc(-c2cncc3ccccc23)cc1] | M + H = 371; $t_{Ret}$ = 1.07 | LCMSBAS1 | 1.3 |
| I-009 | 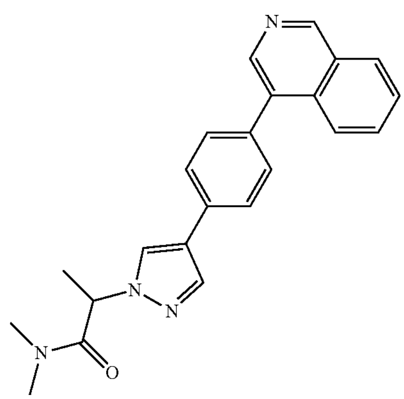 [SMILES: CC(C(=O)N(C)C)n1cc(-c2ccc(-c3cncc4ccccc34)cc2)cn1] | M + H = 371; $t_{Ret}$ = 1.10 | LCMSBAS1 | 1.6 |
| I-010 | 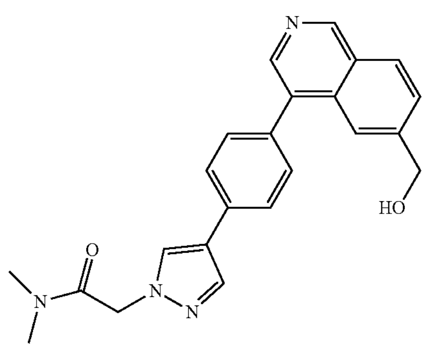 [SMILES: CN(C)C(=O)Cn1cc(-c2ccc(-c3cncc4ccc(CO)cc34)cc2)cn1] | M + H = 387; $t_{Ret}$ = 0.90 | LCMSBAS1 | 1.3 |
| I-011 | 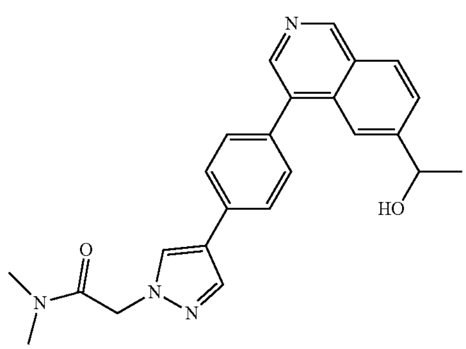 [SMILES: CC(O)c1ccc2cncc(-c3ccc(-c4cnn(CC(=O)N(C)C)c4)cc3)c2c1] | M + H = 401; $t_{Ret}$ = 0.94 | LCMSBAS1 | 1.4 |

TABLE 3-continued
| # | structure | MS (M + H)+; $t_{Ret}$ HPLC [min] | HPLC-MS method | IC$_{50}$ CDK8 [nM] |
|---|---|---|---|---|
| I-012 | 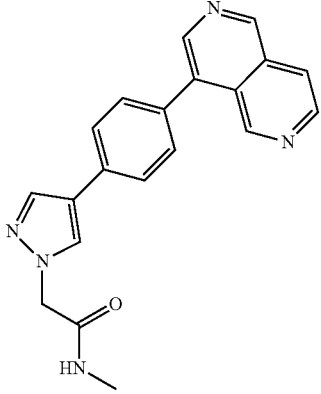 [SMILES: CNC(=O)Cn1cc(-c2ccc(-c3cncc4ccncc34)cc2)cn1] | M + H = 344; $t_{Ret}$ = 0.81 | LCMSBAS1 | 2.5 |
| I-013 | 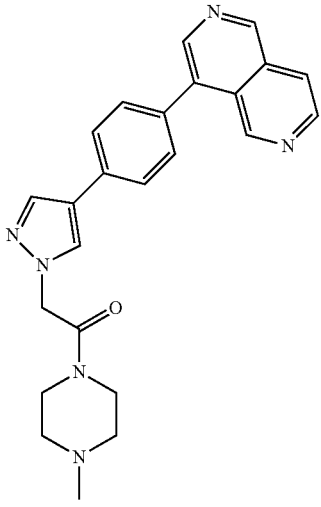 [SMILES: CN1CCN(C(=O)Cn2cc(-c3ccc(-c4cncc5ccncc45)cc3)cn2)CC1] | M + H = 413; $t_{Ret}$ = 0.87 | LCMSBAS1 | 2.7 |
| I-014 | 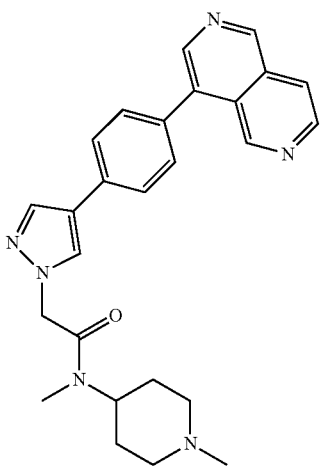 [SMILES: CN1CCC(N(C)C(=O)Cn2cc(-c3ccc(-c4cncc5ccncc45)cc3)cn2)CC1] | M + H = 441; $t_{Ret}$ = 0.97 | LCMSBAS1 | 1.8 |

TABLE 3-continued

| # | structure | MS (M + H)+; $t_{Ret}$ HPLC [min] | HPLC-MS method | IC$_{50}$ CDK8 [nM] |
|---|---|---|---|---|
| I-015 | 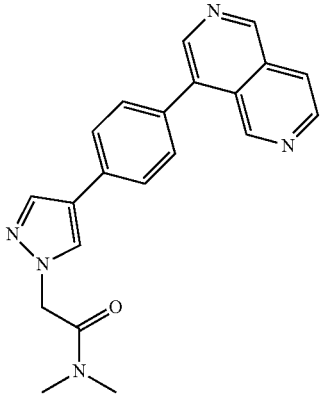 [SMILES: CN(C)C(=O)Cn1cc(-c2ccc(-c3cncc4ccncc34)cc2)cn1] | M + H = 358; $t_{Ret}$ = 0.85 | LCMSBAS1 | 1.8 |
| I-016 | 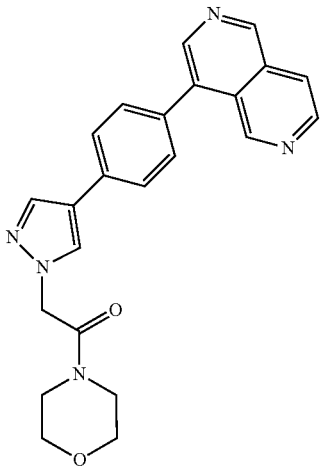 [SMILES: O=C(Cn1cc(-c2ccc(-c3cncc4ccncc34)cc2)cn1)N1CCOCC1] | M + H = 400; $t_{Ret}$ = 0.86 | LCMSBAS1 | 1.6 |
| I-017 | 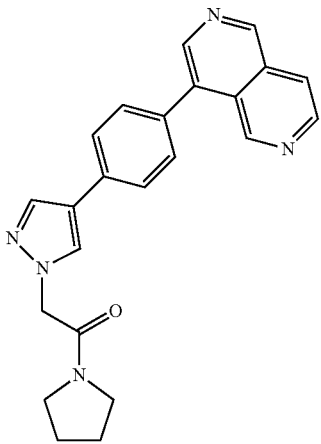 [SMILES: O=C(Cn1cc(-c2ccc(-c3cncc4ccncc34)cc2)cn1)N1CCCC1] | M + H = 384; $t_{Ret}$ = 0.92 | LCMSBAS1 | 1.5 |

The following Examples describe the biological activity of the compounds according to the invention, without restricting the invention to these Examples.

Compounds of formula (I) are characterized by their many possible applications in the therapeutic field.

Particular mention should be made of those applications in which the inhibiting effect on the proliferation of cultivated human tumour cells but also on the proliferation of other cells such as endothelial cells, for example, are involved.

CDK8 Biochemical Assay:

This assay is used to identify compounds which competitively interact with the binding pocket of the CDK8 kinase.

Assay-ready plates (ARPs; Proxiplate-384 PLUS, white, PerkinElmer) with compound solution in 100% DMSO are generated on an Access Labcyte Workstation with the Labcyte Echo 55x. 150 nL of compound solution are transferred per well in 11 concentrations in duplicates with serial 1:5 dilutions. The final DMSO concentration in the assay is 1%.

5 nM (final assay concentration) CDK8/cyclin C, 2 nM (final assay concentration) Biotin anti-His Tag Antibody and 2 nM (final assay concentration) LanthaScreen Eu-Streptavidin are mixed in assay buffer (50 mM HEPES pH 7.3, 10 mM $MgCl_2$, 1 mM EGTA, 0.01% Brij-35, 0.05% BSA, 1 mM DTT) prior to use and kept at room temperature.

The assay runs on a fully automated robotic system. 10 µL of CDK8/cyclin C, Biotin anti-His Tag Antibody and LanthaScreen Eu-Streptavidin mix are dispensed into columns 1-24. 5 µL of 10 nM (final assay concentration) Kinase Tracer 236 solution in assay buffer are added to columns 1-23, 5 µL of assay buffer into column 24. Plates are kept at room temperature in a darkened incubator. After 60 min incubation time the signal is measured in a PerkinElmer Envision HTS Multilabel Reader using the TR-FRET specs from PerkinElmer.

Each plate contains 16 wells of a negative control (diluted DMSO instead of test compound; CDK8/cyclin C, Biotin anti-His Tag Antibody and LanthaScreen Eu-Streptavidin mix w Kinase Tracer 236; column 23) and 16 wells of a positive control (diluted DMSO instead of test compound; CDK8/cyclin C, Biotin anti-His Tag Antibody and LanthaScreen Eu-Streptavidin mix w/o Kinase Tracer 236; column 24). A known inhibitor of CDK8/cyclin C binding is used as internal control. $IC_{50}$ values are calculated and analyzed in the MEGALAB $IC_{50}$ application using a 4 parametric logistic model.

Tables 4 shows the $IC_{50}$ values of example compounds determined using the above assay.

pSTAT1 Ser727 Surefire Assay

This assay quantifies the phosphorylation of STAT1 at S727 as measure of cellular CDK8 activity in NK-92MI cells (ATCC CRL-2408). The cells are split three times a week 1:2 in MEM alpha (Gibco, 22561-054), 12.5% FCS, 12.5% Horse Serum, 0.2 mM Inositol, 0.02 mM folic acid, 0.1 mM mercaptoethanol. The following Surefire assay reagents (PerkinElmer) are required: Stat1 (p-Ser727) TGR-CUS82905, Protein A Acceptor beads 6760137M, 5 mg/mL and AlphaScreen Streptavidin-coated Donor Beads 6760002, 5 mg/mL. The preparation of assay reagents is as follows: one tablet of complete Mini, Proteaseinhibitor Cocktail, Roche #11836170001, is dissolved in 2 mL water and stored at −20° C. 5× Lysis buffer is diluted 5-fold in water and protease-inhibitor is added (400 µL/10 mL lysisbuffer). The phospho-antibody is consecutively diluted 1:50 in dilution buffer and then 1:88 in Reaction Buffer (4400-fold). Immediately prior to use, the activation buffer is diluted 5-fold in Reaction buffer and then the ProteinA Acceptor beads are diluted 50-fold in this Acceptor mix. Immediately prior to use, the Streptavidin Donor beads are diluted 30-fold in Dilution buffer. A 5-fold serial dilution of compounds in DMSO is made on the Echo Access 2 in 384 Labcyte cell culture plates. 60 µL NK-92MI cells (1,000,000 cells/mL) with a viability >80% are added per well. The final DMSO concentration per well is 0.1%. After incubation at 37° C. over night 0.6 µL IFNβ (final conc. 100 U/mL) are added per well on the Echo Access 3 Echo-Protocol (Human IFNβ 1a, PBL Assay Science).

After an incubation at 37° C. for 1 h the medium is removed and cells washed twice with PBS with 10 min centrifugation before any liquid removal. Then 12 µL/well Lysis buffer is added followed by an incubation at RT with shaking for 10 min. The plates are centrifuged 5 min, then 4 µL per well of supernatant is transferred to a 384-well Proxiplate. 5 µL Acceptor Mix are added to each well and incubated for 2 h at room temperature. 3 µL of Donor mix are added to each well under subdued light followed by a 2 h incubation at room temperature in the dark. The signal is read on an Envision using 384 AlphaScreen settings for Proxi plates.

The results are computed using the following procedure: % CTRL is calculated as value of the test compound/value of the negative control (DMSO) multiplied by 100. There is always one negative control. $IC_{50}$ values are computed from the % CTRL results using a 4 parametric logistic model.

Perforin Secretion Assay

60000 NK-92MI cells (ATCC CRL-2408) per well are seeded in MEM Alpha (Gibco, Cat #22561), 12.5% FBS, 12.5% Horse Serum (Gibco, Cat #16050-130), 0.2 mM Inositol, (1:2500)(Sigma, Cat #17508), 0.02 mM folic acid (1:5000)(Sigma, Cat #F8758), fresh: 0.1 mM mercaptoethanol in PBS (1:550)(Gibco, Cat #21985-023; PBS: Gibco, Cat #21985-023) in a 96 well assay plates (Costar, Cat #3599). Inhibitors are diluted in medium including all supplements and added to the cells to achieve a final volume of 200 µL per well. The assay plates are incubated at 37° C. at 5% $CO_2$ for 24 h. After 24 h the assay plates are centrifuged and the supernatant is used in a commercial available perforin ELISA assay (Mabtech AB, Cat #3465-1HP-10). 25 µL of supernatant is used in the ELISA as described in the manual. To acquire the result of the ELISA assay a SpectraMax, Molecular Devices Reader is used. $IC_{50}$ values for both readout formats are calculated and analyzed in the MEGALAB $IC_{50}$ application.

The CDK8 inhibitors according to the invention show an increase of Perforin secretion using this assay.

Cytotox Assays (Cell Proliferation Assays)

Two different types of proliferation assays were performed: 2D and 3D cytotox or proliferation assay. The term cytotox assay is used in case no anti-proliferative effect is awaited by inhibition of CDK8 in the respective cell lines (A549, NK92, B16-F10, 4T-1 and CT26 wt). Any observed anti-proliferative effect might be explainable due to off-target effects of the inhibitors. It is the aim to achieve high $IC_{50}$ values (e.g. $IC_{50}$>10000 nM). The term proliferation assay is in use to screen for sensitive cell lines which respond on inhibition with a CDK8 inhibitor (for example MV-4-11B).

In each described assay the readout can be either performed by Alamar Blue (Serotec), Presto Blue (Invitrogen) or Cell Titer Glo reagent. In case of Alamar Blue or Presto Blue 20 µL substrate is added on the last day of the assay to each well, incubated for up to 7 h at 37° C. and fluorescence is measured at 595 nm emission on a PerkinElmer Envision MultiLabel Reader using 531 nm excitation light. In case of Cell Titer Glo reagent 30 µL is added at the last day of the assay to each well, incubated for 10-30 min at room temperature (with agitation) and luminescence is measured on a PerkinElmer Envision MultiLabel Reader using standard luminescence read out.

$IC_{50}$ values for both readout formats are calculated and analyzed in the MEGALAB $IC_{50}$ application using a 4 parametric logistic model.

The 2D cell assay is used for A549 (lung), and the suspension cells NK-92MI (immortal human NK cells) and MV-4-11-B (human AML). In case of the 2D assay cells are seeded at cell line specific density at day one in flat bottom 96 well microtiter plates in 180 µL cell line specific medium. A549 cells (ATCC CCL-185) are seeded at a density of 2000 cells per well in RPMI medium plus 10% Fetal Calf Serum (FCS), non-essential amino acids (NEAA), 1% sodium pyruvate, Penstrep; NK-92MI cells (CRL-2408) are seeded at a density of 5000 cells per well in MEM alpha no nucleosides plus 12.5% FCS, 20 µM myo-inositol, 200 µM folic acid, 100 µM beta-mercaptoethanol, 12.5% Horse Serum, Penstrep. MV-4-11-B cells (ATCC CRL-9591) are seeded at a density of 10000 cells per well in RPMI plus 20% FCS, 50 µM beta-mercaptoethanol, Penstrep. At day 2 after seeding 20 µL of the serial diluted test compounds are added to the cells. Compounds are diluted in medium plus 1% DMSO to a final start concentration between 10-100 µM in the assay. 12 dilution steps with a dilution factor of 1:3 are used in the dilution scheme. Cells are incubated with compounds for three days. In all assays (3D, clonogenic and 2D assay) cells are incubated in a humidified, $CO_2$-controlled incubator at 37° C. Evaluation of all Alamar Blue, Presto Blue and Cell Titer Glo assays is done at day 5 after seeding.

The 3D cell cytotox assays are performed with B16-F10 (murine melanoma), 4T1 (murine breast cancer) and CT26 wt (murine colon cancer) cells on poly(2)-hydroxyethyl-methacrylate coated plates. The coating blocks cells to adhere on the surface and results in growth and clustering of the cells in 3-dimensional (3D) structures. In case of the 3-D proliferation assay the microtiter plates were coated with poly(2)-hydroxyethylmethacrylate. 500 cells of either B16-F10 cells (ATCC: CRL-6475) or CT26 wt cells (CRL-2638) are seeded in DMEM plus 10% Fetal Calf Serum (FCS) or 4T1 cells (CRL-2539) are seeded in RPMI medium plus 10% Fetal Calf Serum (FCS) and grown for five days. On the first day cells are seeded, on day one different concentrations of the compound are added and on day six Alamar Blue (Serotec) is added and fluorescence measured as described underneath.

Therapeutic Use

Due to their biological properties the compounds of the invention, their tautomers, racemates, enantiomers, diastereomers, mixtures thereof and the salts of all the above-mentioned forms may be suitable for treating diseases characterised by excessive or abnormal cell proliferation such as cancer.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas,

Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery.

Of course, the above also includes the use of the compounds of the invention in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Combinations with Other Active Substances

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Therapeutic agents (=cytostatic and/or cytotoxic active substances) which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/ immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3× BCMA, CD3×CD33, CD3×CD19, PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

Most preferred are combinations with IAP activators, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19, PSMA×CD3) and tumor vaccines.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation and methods of preparing, the compounds of the invention for the combined use with the above combination partners. Also included are the preparation, and methods of preparing, the above-mentioned combination partners for the combined use with the compounds of the invention.

Furthermore, the invention also encompasses kits comprising at least one compound of the invention and one or more other components selected from the group consisting of other drugs used for the treatment of the diseases and disorders as described above, and devices as described below.

Formulations

Suitable preparations include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, agents for delaying release, such as carboxymethyl cellulose, cellulose acetate phthalate, or polyvinyl acetate, carriers, adjuvants, surfactants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 1 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, the route of administration, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

A)

| Tablets | per tablet |
| --- | --- |
| active substance according to formulae (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
| --- | --- |
| active substance according to formulae (I)) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

C)

| Tablets | per tablet |
| --- | --- |
| active substance according to formulae (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

D)

| Ampoule solution | |
| --- | --- |
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I)

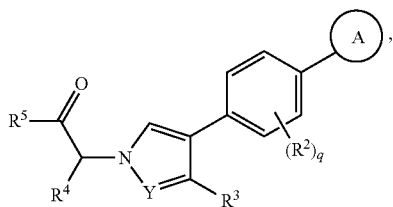
(I)

wherein
ring system A is selected from the group consisting of A1 and A2

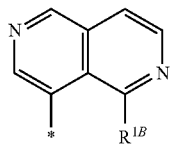
A1

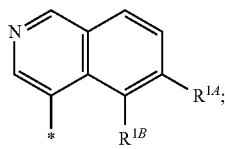
A2

$R^{1A}$ is selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;

each $R^{1B}$ is hydrogen;

each $R^2$ is independently selected from the group consisting of halogen, $C_{1-4}$alkyl, $C_{1-4}$haloalkyl and $C_{1-4}$alkoxy;

q has the value 0;

Y is N;

$R^3$ is selected from the group consisting of hydrogen, halogen, $C_{1-4}$alkyl and $C_{1-4}$haloalkyl;

$R^4$ is selected from the group consisting of hydrogen and $C_{1-4}$alkyl;

$R^5$ is selected from the group consisting of —$NR^{5A}R^{5B}$, —$OR^{5C}$ and $R^{5D}$;

$R^{5A}$, $R^{5B}$ and $R^{5C}$, each independently of one another, denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

each $R^{b1}$ is independently selected from among —$OR^{c1}$, —$NR^{c1}R^{c1}$, halogen, —CN, —$C(O)R^{c1}$, —$C(O)OR^{c1}$, —$C(O)NR^{c1}R^{c1}$, —$S(O)_2R^{c1}$, —$S(O)_2 NR^{c1}R^{c1}$, —$NHC(O)R^{c1}$, —$N(C_{1-4}alkyl)C(O)R^{c1}$ and the bivalent substituent =O, while =O may only be a substituent in non-aromatic ring systems;

each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

or $R^{5A}$ together with $R^4$ or $R^{5C}$ together with $R^4$ is $C_{1-5}$alkylene and $R^{5B}$ is selected from among hydrogen and $C_{1-4}$alkyl;

$R^{5D}$ denotes a 3-10 membered nitrogen containing heterocyclyl linked via a nitrogen atom and optionally substituted by one or more, identical or different $R^{b2}$ and/or $R^{c2}$;

each $R^{b2}$ is independently selected from among —$OR^{c1}$, —$NR^{c1}R^{c1}$, halogen, —CN, —$C(O)R^{c2}$, —$C(O)OR^{c2}$, —$C(O)NR^{c2}R^{c2}$, —$S(O)_2R^{c2}$, —$S(O)_2 NR^{c2}R^{c2}$, —$NHC(O)R^{c2}$, —$N(C_{1-4}alkyl)C(O)R^{c2}$ and the bivalent substituent =O;

each $R^{c2}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;

or a salt thereof.

2. The compound according to claim 1, wherein ring system A is A1

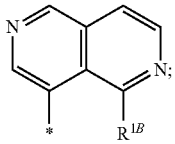
A1

$R^{1B}$ is hydrogen;

or a salt thereof.

3. The compound according to claim 1, wherein ring system A is A2

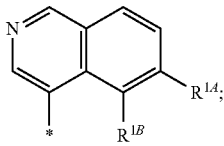
A2

$R^{1A}$ is independently selected from the group consisting of hydrogen, halogen, $C_{1-4}$alkyl, $C_{1-4}$haloalkyl, $C_{1-4}$alkoxy, hydroxy-$C_{1-4}$alkyl, $C_{1-4}$alkoxy-$C_{1-4}$alkyl, —CN and 5-6 membered heteroaryl;

$R^{1B}$ is hydrogen;

or a salt thereof.

4. The compound according to claim 3, wherein ring system A is A2

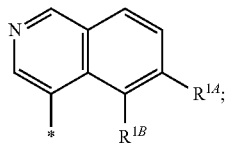

A2

$R^{1A}$ is independently selected from the group consisting of hydrogen and hydroxy-$C_{1-4}$alkyl;
$R^{1B}$ is hydrogen;
or a salt thereof.

5. The compound according to claim 1, wherein
$R^3$ is selected from the group consisting of hydrogen, halogen and $C_{1-4}$alkyl;
or a salt thereof.

6. The compound according to claim 1, wherein
$R^4$ is selected from the group consisting of hydrogen and $C_{1-4}$alkyl;
$R^5$ is —$OR^{5C}$;
$R^{5C}$ denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
each $R^{b1}$ is independently selected from among —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2$ N$R^{c1}R^{c1}$, —NHC(O)$R^{c1}$, —N($C_{1-4}$alkyl)C(O)$R^{c1}$ and the bivalent substituent =O, while =O may only be a substituent in non-aromatic ring systems;
each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5C}$ together with $R^4$ is $C_{1-5}$alkylene;
or a salt thereof.

7. The compound according to claim 6, wherein
$R^4$ is selected from the group consisting of hydrogen and $C_{1-4}$alkyl;
$R^5$ is —$OR^{5C}$;
$R^{5C}$ denotes hydrogen or $C_{1-6}$alkyl;
or
$R^{5C}$ together with $R^4$ is $C_{1-5}$alkylene;
or a salt thereof.

8. The compound according to claim 1, wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by one or more, identical or different $R^{b1}$ and/or $R^{c1}$, selected from among $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
each $R^{b1}$ is independently selected from among —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2$ N$R^{c1}R^{c1}$, —NHC(O)$R^{c1}$, —N($C_{1-4}$alkyl)C(O)$R^{c1}$ and the bivalent substituent =O, while =O may only be a substituent in non-aromatic ring systems;
each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5A}$ together with $R^4$ is $C_{1-5}$alkylene and $R^{5B}$ is selected from among hydrogen and $C_{1-4}$alkyl;
or a salt thereof.

9. The compound according to claim 8, wherein
$R^4$ is selected from the group consisting of hydrogen and $C_{1-4}$alkyl;
$R^5$ is —$NR^{5A}R^{5B}$;
$R^{5A}$ and $R^{5B}$, each independently of one another, denotes hydrogen or a group, optionally substituted by one or more, identical or different $R^{b1}$ and/or $R^{c1}$, selected from among $C_{1-6}$alkyl and 3-10 membered heterocyclyl;
each $R^{b1}$ is independently selected from among —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2$ N$R^{c1}R^{c1}$, —NHC(O)$R^{c1}$, —N($C_{1-4}$alkyl)C(O)$R^{c1}$ and the bivalent substituent =O, while =O may only be a substituent in non-aromatic ring systems;
each $R^{c1}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or
$R^{5A}$ together with $R^4$ is $C_{1-5}$alkylene and $R^{5B}$ is selected from among hydrogen and $C_{1-4}$ alkyl;
or a salt thereof.

10. The compound according to claim 1, wherein
$R^4$ is selected from the group consisting of hydrogen and $C_{1-4}$ alkyl;
$R^5$ is $R^{5D}$;
$R^{5D}$ denotes a 3-10 membered nitrogen containing heterocyclyl linked via a nitrogen atom and optionally substituted by one or more, identical or different $R^{b2}$ and/or $R^{c2}$;
each $R^{b2}$ is independently selected from among —$OR^{c1}$, —$NR^{c1}R^{c1}$, halogen, —CN, —C(O)$R^{c2}$, —C(O)O$R^{c2}$, —C(O)N$R^{c2}R^{c2}$, —S(O)$_2R^{c2}$, —S(O)$_2$ N$R^{c2}R^{c2}$, —NHC(O)$R^{c2}$, —N($C_{1-4}$alkyl)C(O)$R^{c2}$ and the bivalent substituent =O;
each $R^{c2}$ is independently selected from among hydrogen, $C_{1-6}$alkyl, $C_{2-6}$alkenyl, $C_{2-6}$alkynyl, $C_{1-6}$haloalkyl, $C_{3-7}$cycloalkyl, $C_{4-7}$cycloalkenyl, $C_{6-10}$aryl, 5-10 membered heteroaryl and 3-10 membered heterocyclyl;
or a salt thereof.

11. The compound according to claim 10, wherein
$R^4$ is selected from the group consisting of hydrogen and $C_{1-4}$alkyl;
$R^5$ is $R^{5D}$;
$R^{5D}$ denotes a 5-7 membered nitrogen containing heterocyclyl linked via a nitrogen atom and optionally substituted by one or more, identical or different $R^{b2}$ and/or $R^{c2}$;
each $R^{b2}$ is independently selected from among —$OR^{c1}$, —$NR^{c1}R^{c1}$, halogen, —CN, —C(O)$R^{c2}$, —C(O)OR$^{c2}$, —C(O)NR$^{c2}$R$^{c2}$, —S(O)$_2$R$^{c2}$, —S(O)$_2$NR$^{c2}$R$^{c2}$, —NHC(O)R$^{c2}$, —N(C$_{1-4}$alkyl)C(O)R$^{c2}$ and the bivalent substituent =O;

each R$^{c2}$ is independently selected from among hydrogen, C$_{1-6}$alkyl, C$_{2-6}$alkenyl, C$_{2-6}$alkynyl, C$_{1-6}$haloalkyl, C$_{3-7}$cycloalkyl, C$_{4-7}$cycloalkenyl, C$_{6-10}$aryl, 5-10 membered heteroaryl and 3-10 membered heterocyclyl;

or a salt thereof.

12. A pharmaceutical composition comprising at least one compound of formula (I)—or a pharmaceutically acceptable salt thereof—according to claim 1 and a pharmaceutically acceptable carrier.

13. A pharmaceutical preparation comprising a compound of formula (I)—or a pharmaceutically acceptable salt thereof—according to claim 1 and at least one other cytostatic and/or cytotoxic active substance.

14. The compound according to claim 1, wherein said compound is selected from the group consisting of:

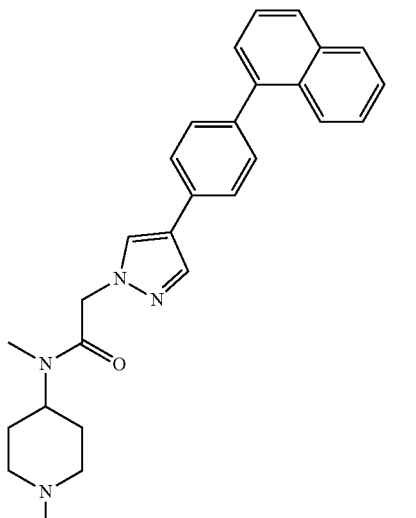

,

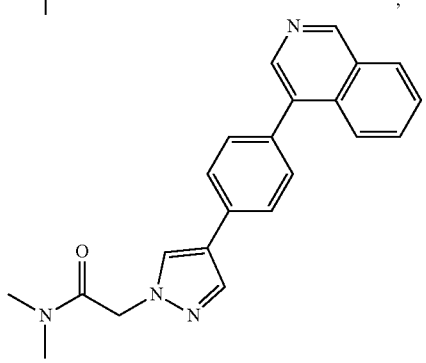

,

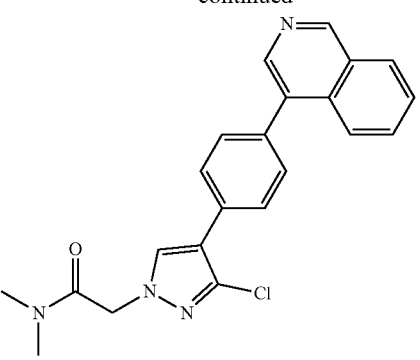

,

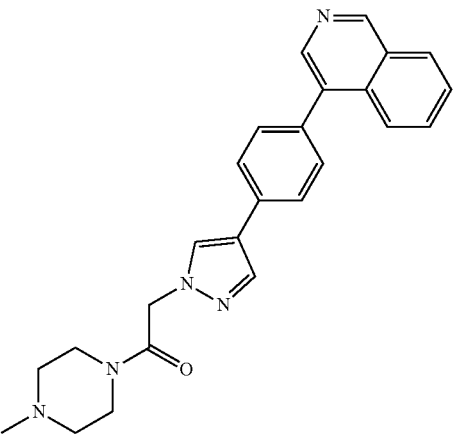

and

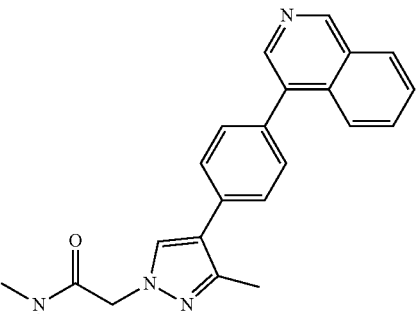

.

* * * * *